(12) United States Patent
Van Hoven et al.

(10) Patent No.: US 9,307,952 B2
(45) Date of Patent: Apr. 12, 2016

(54) METHOD FOR FOCUSING MINIATURE ULTRASOUND TRANSDUCERS

(71) Applicant: Volcano Corporation, San Diego, CA (US)

(72) Inventors: Dylan Van Hoven, Oceanside, CA (US); Jeffrey Brown, Valley Center, CA (US); Paul Douglas Corl, Palo Alto, CA (US); Michael Reiter, San Diego, CA (US)

(73) Assignee: Volcano Corporation, San Diego, CA (US)

( * ) Notice: Subject to any disclaimer, the term of this patent is extended or adjusted under 35 U.S.C. 154(b) by 59 days.

(21) Appl. No.: 14/105,360

(22) Filed: Dec. 13, 2013

(65) Prior Publication Data

US 2014/0178574 A1    Jun. 26, 2014

Related U.S. Application Data

(60) Provisional application No. 61/745,212, filed on Dec. 21, 2012.

(51) Int. Cl.
| | |
|---|---|
| *B05D 5/12* | (2006.01) |
| *A61B 8/12* | (2006.01) |
| *B06B 1/06* | (2006.01) |
| *H01L 41/00* | (2013.01) |
| *H01L 41/22* | (2013.01) |
| *H01L 41/33* | (2013.01) |

(52) U.S. Cl.
CPC ............... *A61B 8/12* (2013.01); *B06B 1/0688* (2013.01); *B06B 2201/76* (2013.01); *H01L 41/00* (2013.01); *H01L 41/22* (2013.01); *H01L 41/33* (2013.01)

(58) Field of Classification Search
USPC .......................................... 427/100; 29/25.35
See application file for complete search history.

(56) References Cited

U.S. PATENT DOCUMENTS

| | | | |
|---|---|---|---|
| 5,243,988 A | 9/1993 | Sieben et al. | |
| 5,488,954 A * | 2/1996 | Sleva et al. ................... | 600/459 |
| 5,546,948 A | 8/1996 | Hamm et al. | |
| 6,321,428 B1 * | 11/2001 | Toda et al. .................. | 29/25.35 |
| 6,641,540 B2 * | 11/2003 | Fleischman et al. .......... | 600/459 |
| 7,830,069 B2 * | 11/2010 | Lukacs et al. ................. | 310/334 |
| 8,847,467 B2 * | 9/2014 | Chaggares ............. | B06B 1/067 310/334 |
| 2014/0180117 A1 | 6/2014 | Dylan Van Hoven et al. | |

* cited by examiner

*Primary Examiner* — Brian K Talbot
(74) *Attorney, Agent, or Firm* — Haynes and Boone, LLP

(57) ABSTRACT

The present disclosure provides methods and apparatus of fabricating a transducer for use in ultrasound imaging. A substrate is provided. The substrate may be a silicon substrate having a first side and a second side opposite the first side. A transducer membrane is formed over the first side of the substrate. The transducer membrane includes a piezoelectric component. A well is formed in the substrate from the second side. A backing material is dispensed onto a first sidewall of the well in a manner so as to create a capillary effect that causes the backing material to wick down the sidewall, across the back side of the substrate exposed by the well, and up a second sidewall of the well. The transducer membrane is deflected so that the transducer membrane has a concave shape.

22 Claims, 15 Drawing Sheets

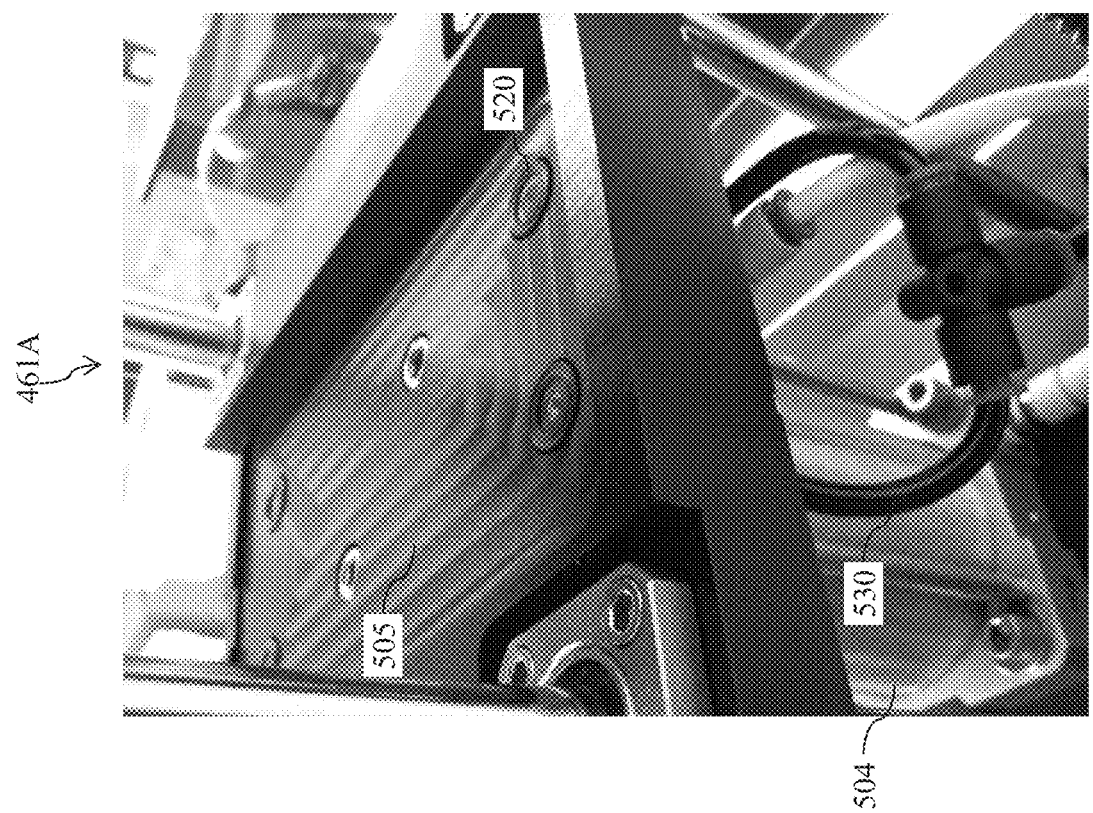

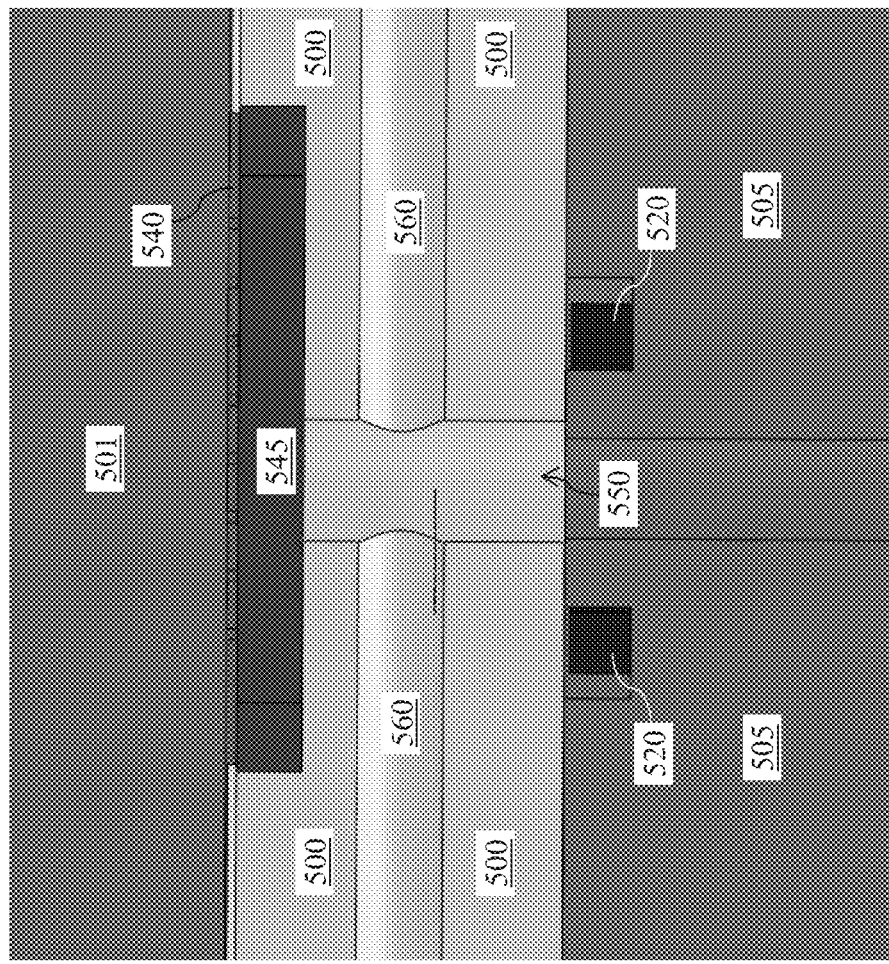

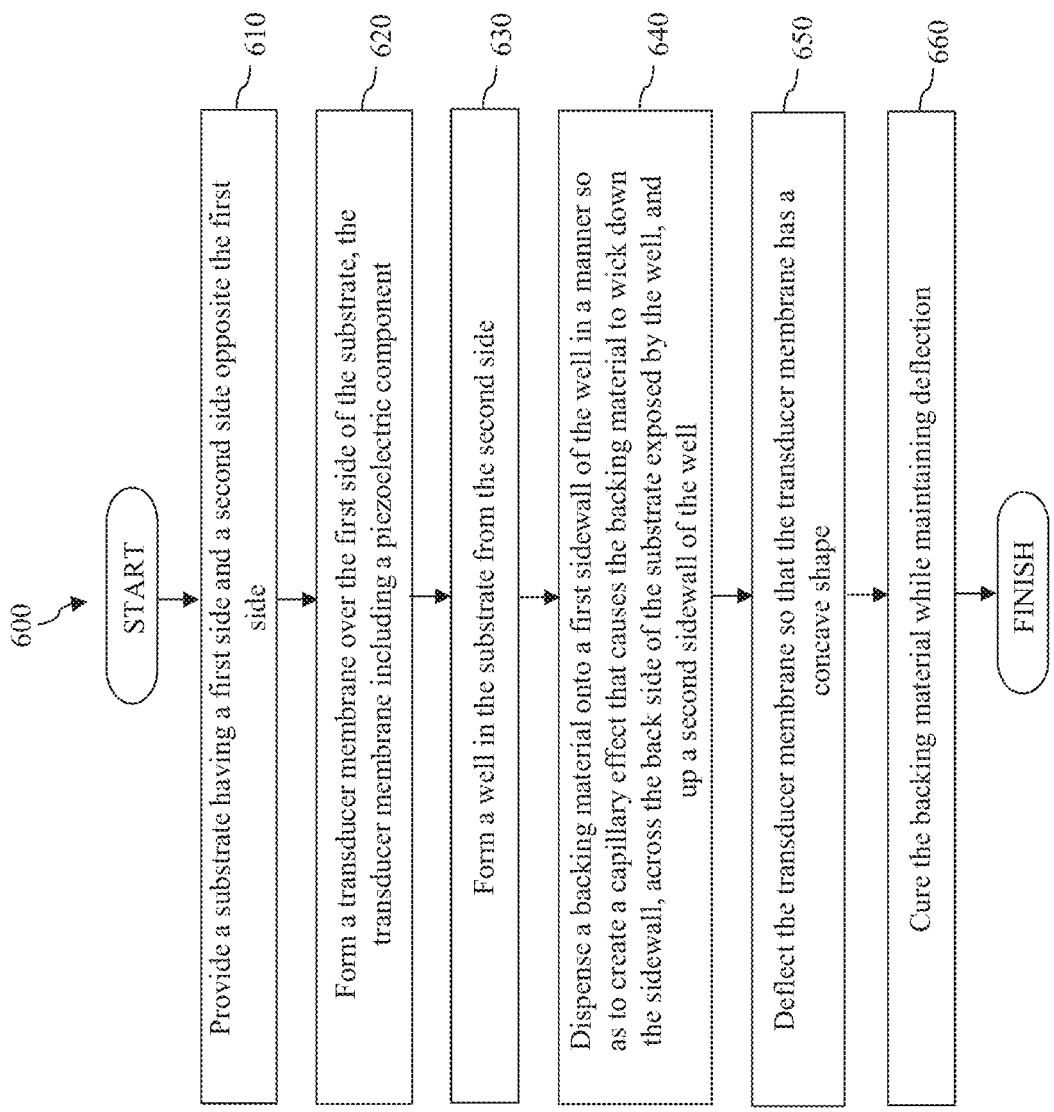

METHOD FOR FOCUSING MINIATURE ULTRASOUND TRANSDUCERS

CROSS-REFERENCE TO RELATED APPLICATIONS

This application claims priority to Provisional Patent Application No. 61/745,212, filed Dec. 21, 2012, and entitled "Method and Apparatus for Focusing Miniature Ultrasound Transducers," the disclosure of which is hereby incorporated by reference in its entirety.

TECHNICAL FIELD

The present disclosure relates generally to ultrasound imaging, and in particular, to a miniature ultrasound transducer, such as a piezoelectric micromachined ultrasound transducer (PMUT), used for intravascular imaging.

BACKGROUND

Intravascular ultrasound (IVUS) imaging is widely used in interventional cardiology as a diagnostic tool for assessing a vessel, such as an artery, within the human body to determine the need for treatment, to guide intervention, and/or to assess its effectiveness. An IVUS imaging system uses ultrasound echoes to form a cross-sectional image of the vessel of interest. Typically, IVUS imaging uses a transducer on an IVUS catheter that both emits ultrasound signals (waves) and receives the reflected ultrasound signals. The emitted ultrasound signals (often referred to as ultrasound pulses) pass easily through most tissues and blood, but they are partially reflected by discontinuities arising from tissue structures (such as the various layers of the vessel wall), red blood cells, and other features of interest. The IVUS imaging system, which is connected to the IVUS catheter by way of a patient interface module, processes the received ultrasound signals (often referred to as ultrasound echoes) to produce a cross-sectional image of the vessel where the IVUS catheter is located.

IVUS catheters typically employ one or more transducers to transmit ultrasound signals and receive reflected ultrasound signals. However, conventional methods and apparatuses for fabricating transducers may not be optimized. For example, conventional methods and apparatuses do not disclose how to shape a thin polymer film into an ultrasound transducer having concave, lens-like geometries in an automated process.

Therefore, while conventional methods and apparatuses of fabricating transducers are generally adequate for their intended purposes, they have not been entirely satisfactory in every aspect.

SUMMARY

Ultrasound transducers are used in intravascular ultrasound (IVUS) imaging to assess medical conditions inside a human body. According to the present disclosure, the fabrication of ultrasound transducers involves shaping a thin polymer film into a concave, lens-like transducer membrane. The polymer film may have piezoelectric properties, which means that electrical charge may be acquired when the polymer film is compressed, twisted, or otherwise distorted. The polymer film is formed over a front side of a substrate. A well is formed from the back side of the substrate. A backing material, such as epoxy, is dispensed into the well. The polymer film is then deflected into having a concave shape.

One aspect of the present disclosure involves a method of fabricating a miniature ultrasound transducer. The method includes: providing a substrate having a first side and a second side opposite the first side; forming a transducer membrane over the first side of the substrate, the transducer membrane including a piezoelectric component; forming a well in the substrate from the second side; dispensing a backing material onto a first sidewall of the well in a manner so as to create a capillary effect that causes the backing material to wick down the sidewall, across the back side of the substrate exposed by the well, and up a second sidewall of the well; and deflecting the transducer membrane so that the transducer membrane has a concave shape.

Another aspect of the present disclosure involves a method of fabricating an ultrasound transducer. The method includes: providing a wafer having a first side and a second side opposite the first side; forming a transducer membrane over the first side of the wafer, the transducer membrane including a piezoelectric component; forming an opening in the wafer from the second side; partially filling the opening with an epoxy material in a manner such that a predetermined amount of head space is reserved in the well; applying air pressure to the transducer membrane from the first side to deflect a portion of the transducer membrane towards the second side; and curing the epoxy material by heat during the applying the air pressure.

Yet another aspect of the present disclosure involves: a method of shaping a transducer. The method includes: providing a wafer having a first side and a second side opposite the first side; forming a multi-layered transducer membrane over the first side of the wafer, one of the layers of the transducer membrane being a piezoelectric layer; forming a well in the wafer, the well being open to the second side; dispensing an epoxy material into a sidewall of the well in a manner so as to induce a capillary effect that causes the well to be partially filled substantially without air bubbles; deflecting the transducer membrane by applying pressurized air from the first side until the transducer membrane achieves an arcuate shape; and curing the epoxy material while the transducer membrane is deflected.

Another aspect of the present disclosure involves a transducer shaping chamber for shaping ultrasound transducers. The transducer shaping chamber includes: a transducer coupon carrier having one or more slots, the one or more slots each being geometrically shaped to hold a transducer coupon having a plurality of ultrasound transducers formed thereon; a first plate disposed over a first side of the transducer coupon carrier; and a second plate disposed over a second side of the transducer coupon carrier, the second side being opposite the first side; wherein the transducer shaping chamber is configured to move the first plate and the second plate toward each other so as to push against the transducer coupon carrier from the first and second sides, respectively, until the transducer coupon carrier has been sealed against the first plate and with the second plate.

One more aspect of the present disclosure involves a system for fabricating an ultrasound transducer. The system includes: a control panel that includes a plurality of control mechanisms configured to set a plurality of fabrication process parameters, the fabrication process parameters being selected from the group consisting of: process pressure, process time, process duration, and process voltage; and a transducer shaping chamber communicatively coupled to the control panel and configured to implement the fabrication process parameters therein in response to instructions from the control panel, the transducer shaping chamber including: a removable part carrier configured to load a transducer coupon having a plurality of transducers formed thereon, the transducers each having a transducer membrane disposed over a well partially filled with an epoxy; a first plate configured to support and seal against the part carrier from a first side, the first plate facing the transducer well; and a second plate configured to support and seal against the part carrier from a second side opposite the first side, the second plate facing toward the transducer membrane; wherein: the first and second plates are configured to be moved toward each other until the part carrier is sealed between the first plate and the second plate; and the transducer shaping chamber is configured to deflect the transducer membrane into an arcuate shape through application of pressurized air.

Another aspect of the present disclosure involves a transducer shaping apparatus for shaping a plurality of ultrasound transducers collectively. The apparatus includes: a bottom plate having an air hole that allows a pressurized air to be delivered into the transducer shaping apparatus; a removable transducer coupon carrier disposed over the bottom plate, the transducer coupon carrier including a slot that is geometrically configured to hold and support a transducer coupon having a plurality of ultrasound transducers formed thereon, and wherein the slot includes an air inlet coupled to the air hole of the bottom plate, the air inlet allowing the pressurized air to be applied to the plurality of transducers collectively; a top plate disposed over the transducer coupon carrier, the top plate being configured to be heated; and wherein the top plate and the bottom plate are configured to be moved toward each other so as to seal against the transducer coupon carrier from opposites sides and seal the transducer coupon carrier therebetween while the pressurized air is applied to the plurality of transducers.

Both the foregoing general description and the following detailed description are exemplary and explanatory in nature and are intended to provide an understanding of the present disclosure without limiting the scope of the present disclosure. In that regard, additional aspects, features, and advantages of the present disclosure will become apparent to one skilled in the art from the following detailed description.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

FIGS. 7-13 are block diagrams and illustrations of a transducer shaping system according to various aspects of the present disclosure.

FIG. 15 is a flowchart illustrating a method for fabricating an ultrasound transducer according to various aspects of the present disclosure.

DETAILED DESCRIPTION

Figure 1:
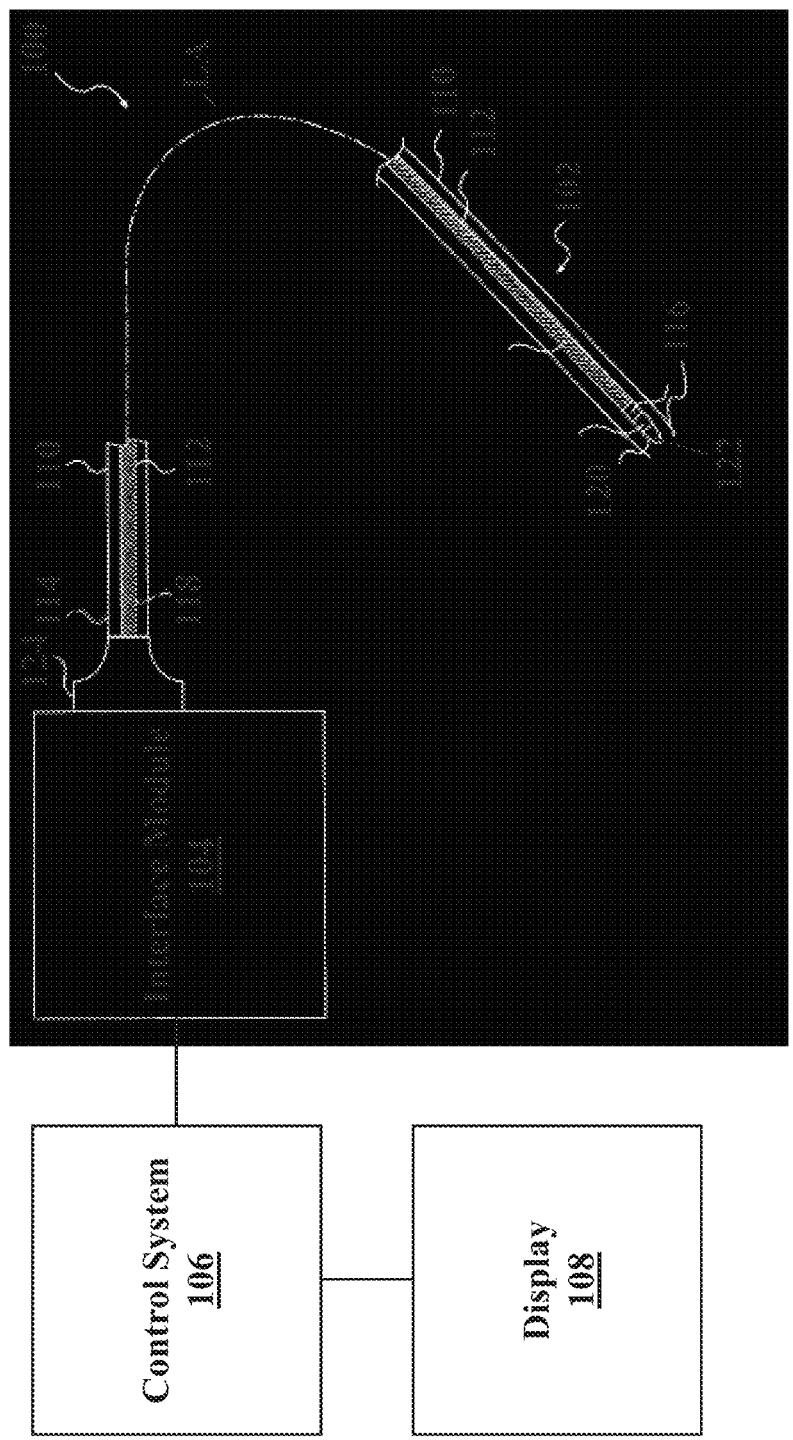
FIG. 1 is a schematic illustration of an intravascular ultrasound (IVUS) imaging system according to various aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. For example, the present disclosure provides an ultrasound imaging system described in terms of cardiovascular imaging, however, it is understood that such description is not intended to be limited to this application, and that such imaging system can be utilized for imaging throughout the body. In some embodiments, the illustrated ultrasound imaging system is a side looking intravascular imaging system, although transducers formed according to the present disclosure can be mounted in other orientations including forward looking. The imaging system is equally well suited to any application requiring imaging within a small cavity. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

There are primarily two types of catheters in common use today: solid-state and rotational. An exemplary solid-state catheter uses an array of transducers (typically 64) distributed around a circumference of the catheter and connected to an electronic multiplexer circuit. The multiplexer circuit selects transducers from the array for transmitting ultrasound signals and receiving reflected ultrasound signals. By stepping through a sequence of transmit-receive transducer pairs, the solid-state catheter can synthesize the effect of a mechanically scanned transducer element, but without moving parts. Since there is no rotating mechanical element, the transducer array can be placed in direct contact with blood and vessel tissue with minimal risk of vessel trauma, and the solid-state scanner can be wired directly to the imaging system with a simple electrical cable and a standard detachable electrical connector.

An exemplary rotational catheter includes a single transducer located at a tip of a flexible driveshaft that spins inside a sheath inserted into the vessel of interest. The transducer is typically oriented such that the ultrasound signals propagate generally perpendicular to an axis of the catheter. In the typical rotational catheter, a fluid-filled (e.g., saline-filled) sheath protects the vessel tissue from the spinning transducer and driveshaft while permitting ultrasound signals to freely propagate from the transducer into the tissue and back. As the driveshaft rotates (for example, at 30 revolutions per second), the transducer is periodically excited with a high voltage pulse to emit a short burst of ultrasound. The ultrasound signals are emitted from the transducer, through the fluid-filled sheath and sheath wall, in a direction generally perpendicular to an axis of rotation of the driveshaft. The same transducer then listens for returning ultrasound signals reflected from various tissue structures, and the imaging system assembles a two dimensional image of the vessel cross-section from a sequence of several hundred of these ultrasound pulse/echo acquisition sequences occurring during a single revolution of the transducer.

FIG. 1 is a schematic illustration of an ultrasound imaging system 100 according to various aspects of the present disclosure. In some embodiments, the ultrasound imaging system 100 includes an intravascular ultrasound imaging system (IVUS). The IVUS imaging system 100 includes an IVUS catheter 102 coupled by a patient interface module (PIM) 104 to an IVUS control system 106. The control system 106 is coupled to a monitor 108 that displays an IVUS image (such as an image generated by the IVUS system 100).

In some embodiments, the IVUS catheter 102 is a rotational IVUS catheter, which may be similar to a Revolution® Rotational IVUS Imaging Catheter available from Volcano Corporation and/or rotational IVUS catheters disclosed in U.S. Pat. No. 5,243,988 and U.S. Pat. No. 5,546,948, both of which are incorporated herein by reference in their entirety. The catheter 102 includes an elongated, flexible catheter sheath 110 (having a proximal end portion 114 and a distal end portion 116) shaped and configured for insertion into a lumen of a blood vessel (not shown). A longitudinal axis LA of the catheter 102 extends between the proximal end portion 114 and the distal end portion 116. The catheter 102 is flexible such that it can adapt to the curvature of the blood vessel during use. In that regard, the curved configuration illustrated in FIG. 1 is for exemplary purposes and in no way limits the manner in which the catheter 102 may curve in other embodiments. Generally, the catheter 102 may be configured to take on any desired straight or arcuate profile when in use.

A rotating imaging core 112 extends within the sheath 110. The imaging core 112 has a proximal end portion 118 disposed within the proximal end portion 114 of the sheath 110 and a distal end portion 120 disposed within the distal end portion 116 of the sheath 110. The distal end portion 116 of the sheath 110 and the distal end portion 120 of the imaging core 112 are inserted into the vessel of interest during operation of the IVUS imaging system 100. The usable length of the catheter 102 (for example, the portion that can be inserted into a patient, specifically the vessel of interest) can be any suitable length and can be varied depending upon the application. The proximal end portion 114 of the sheath 110 and the proximal end portion 118 of the imaging core 112 are connected to the interface module 104. The proximal end portions 114, 118 are fitted with a catheter hub 124 that is removably connected to the interface module 104. The catheter hub 124 facilitates and supports a rotational interface that provides electrical and mechanical coupling between the catheter 102 and the interface module 104.

The distal end portion 120 of the imaging core 112 includes a transducer assembly 122. The transducer assembly 122 is configured to be rotated (either by use of a motor or other rotary device or manually by hand) to obtain images of the vessel. The transducer assembly 122 can be of any suitable type for visualizing a vessel and, in particular, a stenosis in a vessel. In the depicted embodiment, the transducer assembly 122 includes a piezoelectric micromachined ultrasonic transducer ("PMUT") transducer and associated circuitry, such as an application-specific integrated circuit (ASIC). An exemplary PMUT used in IVUS catheters may include a polymer piezoelectric membrane, such as that disclosed in U.S. Pat. No. 6,641,540, hereby incorporated by reference in its entirety. The PMUT transducer can provide greater than 100% bandwidth for optimum resolution in a radial direction, and a spherically-focused aperture for optimum azimuthal and elevation resolution.

The transducer assembly 122 may also include a housing having the PMUT transducer and associated circuitry disposed therein, where the housing has an opening that ultrasound signals generated by the PMUT transducer travel through. In yet another alternative embodiment, the transducer assembly 122 includes an ultrasound transducer array (for example, arrays having 16, 32, 64, or 128 elements are utilized in some embodiments).

The rotation of the imaging core 112 within the sheath 110 is controlled by the interface module 104, which provides user interface controls that can be manipulated by a user. The interface module 104 can receive, analyze, and/or display information received through the imaging core 112. It will be appreciated that any suitable functionality, controls, information processing and analysis, and display can be incorporated into the interface module 104. In an example, the interface module 104 receives data corresponding to ultrasound signals (echoes) detected by the imaging core 112 and forwards the received echo data to the control system 106. In an example, the interface module 104 performs preliminary processing of the echo data prior to transmitting the echo data to the control system 106. The interface module 104 may perform amplification, filtering, and/or aggregating of the echo data. The interface module 104 can also supply high- and low-voltage DC power to support operation of the catheter 102 including the circuitry within the transducer assembly 122.

In some embodiments, wires associated with the IVUS imaging system 100 extend from the control system 106 to the interface module 104 such that signals from the control system 106 can be communicated to the interface module 104 and/or visa versa. In some embodiments, the control system 106 communicates wirelessly with the interface module 104. Similarly, it is understood that, in some embodiments, wires associated with the IVUS imaging system 100 extend from the control system 106 to the monitor 108 such that signals from the control system 106 can be communicated to the monitor 108 and/or vice versa. In some embodiments, the control system 106 communicates wirelessly with the monitor 108.

FIGS. 2-3, 4-5, and 11 are diagrammatic fragmentary cross-sectional side views of a miniature ultrasound transducer 200 at different stages of fabrication in accordance with various aspects of the present disclosure. FIGS. 2-3, 4-5, and 11 have been simplified for the sake of clarity to better understand the inventive concepts of the present disclosure.

The ultrasound transducer 200 can be included in the IVUS imaging system 100 of FIG. 1, for example in the transducer assembly 122. The ultrasonic transducer 200 has a small size and achieves a high resolution, so that it is well suited for intravascular imaging. In some embodiments, the ultrasonic transducer 200 has a size on the order of tens or hundreds of microns, can operate in a frequency range between about 1 mega-Hertz (MHz) to about 135 MHz, and can provide sub 50 micron resolution while providing depth penetration of at least 10 millimeters (mm). Furthermore, the ultrasonic transducer 200 is also shaped in a manner to allow a developer to define a target focus area based on a deflection depth of a transducer aperture, thereby generating an image that is useful for defining vessel morphology, beyond the surface characteristics. The various aspects of the ultrasound transducer 200 and its fabrication are discussed in greater detail below.

In the depicted embodiment, the ultrasound transducer 200 is a piezoelectric micromachined ultrasound transducer (PMUT). In other embodiments, the transducer 200 may include an alternative type of transducer. Additional features can be added in the ultrasound transducer 200, and some of the features described below can be replaced or eliminated for additional embodiments of the ultrasound transducer 200.

Figure 2:
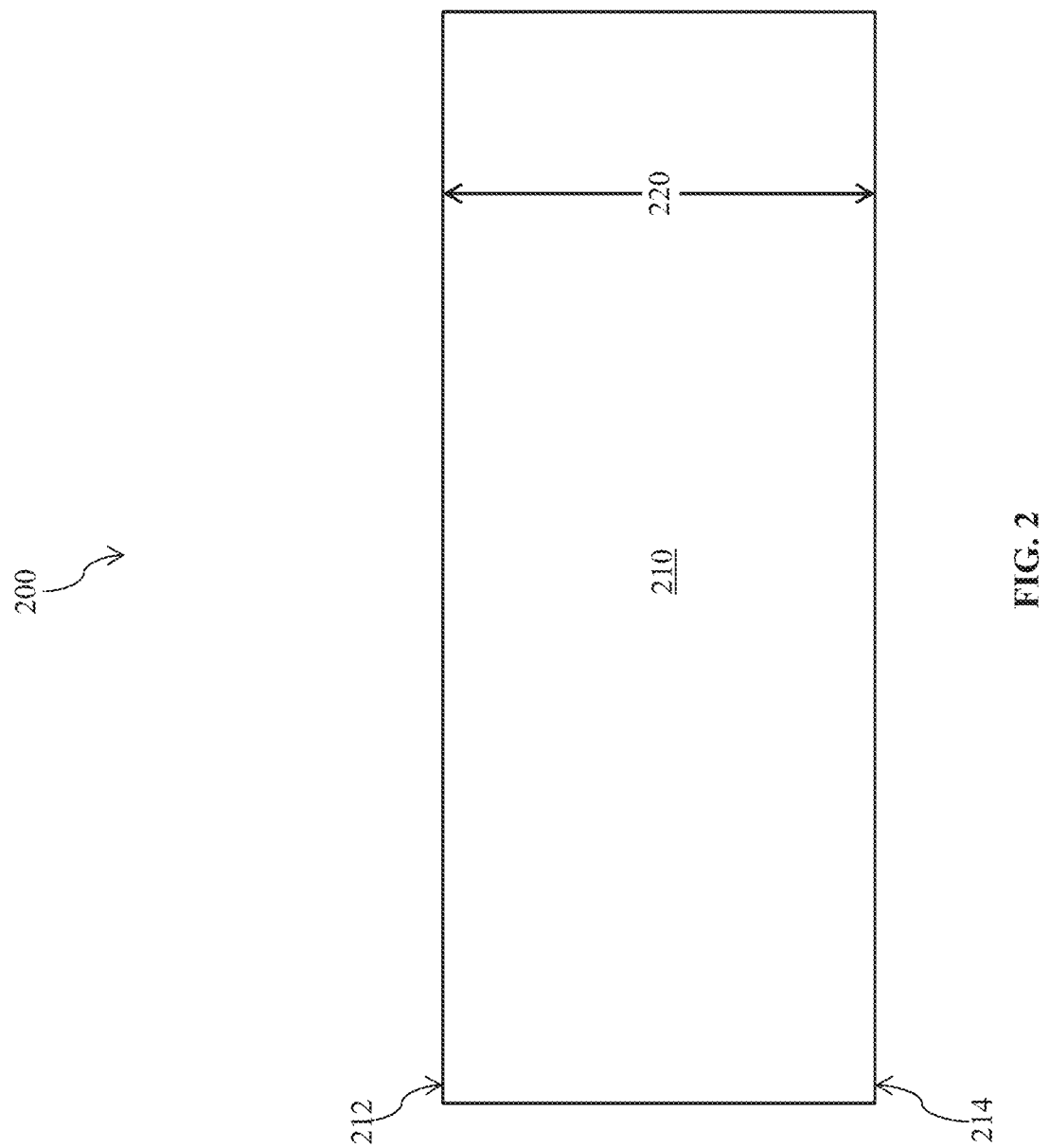
FIGS. 2-3, 5-6 and 14 are diagrammatic cross-sectional side views of an ultrasound transducer at different stages of fabrication according to various aspects of the present disclosure.

Referring now to FIG. 2, the transducer 200 includes a substrate 210 (also referred to as a wafer). The substrate 210 has a surface 212 and a surface 214 that is opposite the surface 212. The surface 212 may also be referred to as a front surface or a front side, and the surface 214 may also be referred to as a back surface or a back side. In the depicted embodiment, the substrate 210 is a silicon microelectromechanical system (MEMS) substrate. The substrate 210 includes another suitable material depending on design requirements of the PMUT transducer 200 in alternative embodiments.

The substrate 210 may also include various layers that are not separately depicted and that can combine to form electronic circuitry, which may include various microelectronic elements. These microelectronic elements may include: transistors (for example, metal oxide semiconductor field effect transistors (MOSFET), complementary metal oxide semiconductor (CMOS) transistors, bipolar junction transistors (BJT), high voltage transistors, high frequency transistors, p-channel and/or n-channel field effect transistors (PFETs/NFETs)); resistors; diodes; capacitors; inductors; fuses; and/or other suitable elements. The various layers may include high-k dielectric layers, gate layers, hard mask layers, interfacial layers, capping layers, diffusion/barrier layers, dielectric layers, conductive layers, other suitable layers, or combinations thereof. The microelectronic elements could be interconnected to one another to form a portion of an integrated circuit, such as a logic device, memory device (for example, a static random access memory (SRAM)), radio frequency (RF) device, input/output (I/O) device, system-on-chip (SoC) device, other suitable types of devices, or combinations thereof.

A thickness 220 of the substrate 210 is measured between the surface 212 and the surface 214. In some embodiments, the thickness 220 is in a range from about 100 microns (um) to about 600 um. In the illustrated embodiment, the substrate 210 is a part of a wafer that includes a plurality of mass-produced miniature transducers. These miniature transducers are substantially similar to the transducer 200 and are simultaneously fabricated with the transducer 200 using the same fabrication processes discussed herein. For the sake of simplicity, only one of these miniature transducers 200 is described in detail below, but it is understood that the same discussions apply to the other miniature transducers on the wafer as well.

Figure 3:
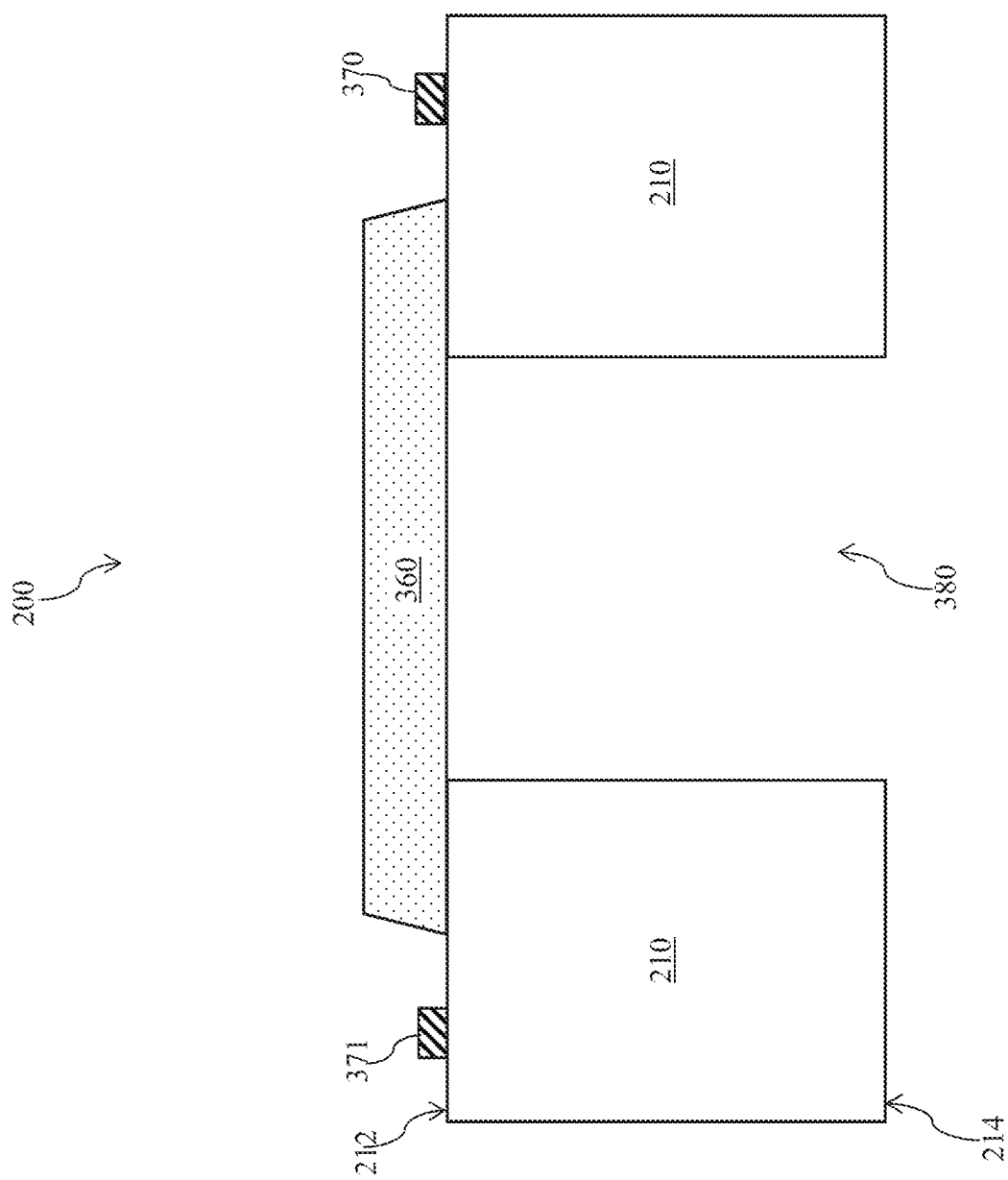

Referring now to FIG. 3, a transducer membrane 360 is formed over the front surface 212 of the substrate 210. The transducer membrane 360 includes a polymer material, for example a piezoelectric polymer material. In various embodiments, the piezoelectric material may include polyvinylidene fluoride (PVDF) or its co-polymers, polyvinylidene fluoride-trifluoroethylene (PVDF-TrFE), or polyvinylidene fluoride-tetrafluoroethylene (PVDF-TFE). Alternatively, polymers such as PVDF-CTFE or PVDF-CFE may be used.

In some embodiments, the polymer material of the transducer membrane 360 is formed to have a high β phase crystallinity. β phase crystallinity is important when using PVDF-TrFE in piezoelectric applications, as the β phase crystallinity is a crystalline phase that is capable of retaining permanent polarization, which is needed for a semi crystalline polymer to become piezoelectric. A method to form a polymer film with high β phase crystallinity using a coating process (such as spin coating) is described in Provisional U.S. Patent Application 61/745,091 to Dylan Van Hoven, filed on December 21, entitled "Preparation and Application of a Piezoelectric Film for an Ultrasound Transducer", the contents of which are herein incorporated by reference in its entirety.

In addition to the polymer material (e.g., the PVDF-TrFE material), the transducer membrane 360 may also include conductive layers that provide electrical access to the transducer membrane 360. These conductive layers may have a metal composition and may be formed on either side (i.e., top and bottom sides) of the polymer material, such that at least a portion of the polymer material is sandwiched between the conductive layers. In various embodiments, the conductive layers are formed through one or more deposition processes (e.g., chemical vapor deposition (CVD), physical vapor deposition (PVD), atomic layer deposition (ALD), or combinations thereof) followed by one or more lithography patterning processes. In some embodiments, the transducer membrane may further include a dielectric support layer (e.g., an oxide layer). The various layers of the transducer membrane 360 and the fabrication thereof are described in more detail in Provisional U.S. Patent Application 61/740,998 to Cheryl R. Rice, filed on December 21, entitled "Method of Fabricating the MEM's FACT Transducer", the contents of which are herein incorporated by reference in its entirety. For reasons of simplicity, the structural details of the transducer membrane are not specifically shown herein.

Pad metals 370-371 may also be formed over the surface 212 of the substrate 210. The pad metals 370-371 may be formed by depositing a layer of metal over the substrate 210 and thereafter patterning the layer of metal in a lithography process. The pad metals 370-371 are each electrically coupled to a respective one of the conductive layers of the transducer membrane 360. As such, the pad metals 370-371 may serve as electrodes for the transducer 200, so that electrical connections may be established between the transducer 200 and external devices such as electronic circuitry (not illustrated herein). The electronic circuitry can excite the transducer membrane 360 so that it generates sound waves, particularly sound waves in an ultrasound range.

A well 380 is formed in the substrate 210 from the back side 214. The well 380 may also be referred to as an opening, a void, or a recess. In some embodiments, the well 380 is formed up to the bottom surface of the transducer membrane 360. In other words, a portion of the transducer membrane 360 is exposed by the well 380. In some embodiments, the well 380 is formed by an etching process, for example a deep reactive ion etching (DRIE) process. The well 380 forms an aperture of the transducer 200. Thereafter, the surface around the individual transducer 200 may be etched to define a singulated form factor for the device.

The well 380 is then filled with an epoxy material to dampen sound coming off the back side of the transducer 200 and to also permanently hold the transducer membrane 360 into a lens-like shape. In some embodiments, the epoxy material is dispensed into the well 380 manually. In other embodiment, the epoxy material is dispensed into the well 380 automatically via an x, y, z automated stage. For example, in some embodiments, the D-583 or D-585 DispenseMate Benchtop Dispensing Systems from Nordson Asymtek may be used. These dispensing systems may implement a closed-loop DC servo motion control and/or a Jet-on-the-fly jet dispensing capability, as well as software for intuitive user programming. In some cases, these dispensing systems may have integrated height sensors and/or digital gauges for easy setup and greater programming accuracy.

Figure 4:
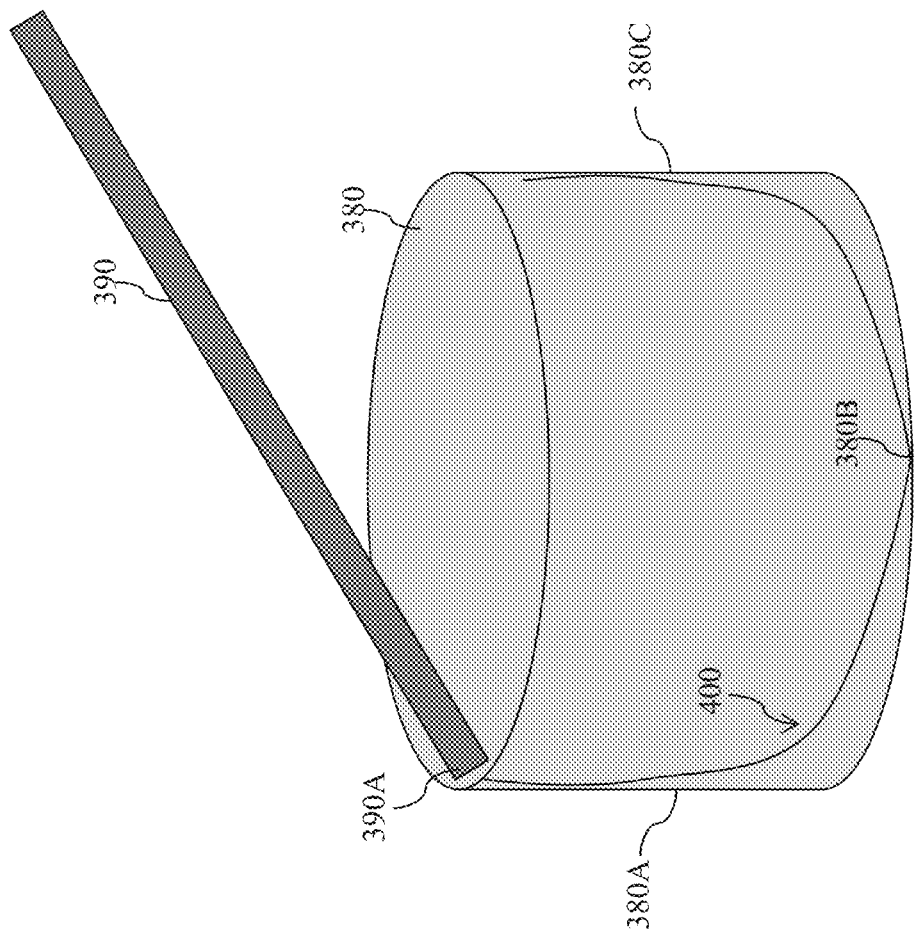
FIG. 4 is a diagrammatic illustration of how a backing material is dispensed into a well of the ultrasound transducer according to various aspects of the present disclosure.

FIG. 4 is a simplified diagrammatic illustration of how the epoxy material is dispensed into the well 380. It is understood that the well 380 illustrated in FIG. 4 is flipped upside-down (from FIG. 3), such that the side 212 in FIG. 3 is located near the bottom of FIG. 4, and the side 214 in FIG. 3 is located near the top of FIG. 4. As discussed above, the transducer 200 herein is a miniature transducer whose small dimensions may make its well 380 difficult to fill. For example, conventional processes used to fill such wells as small as the well 380 may lead to air bubbles being trapped in the well, thereby degrading the well's performance. To overcome these problems, the present disclosure involves a novel well-filling process (discussed below in more detail) that utilizes a capillary effect to ensure the well 380 is filled without the problems associated with conventional methods.

In some embodiments, a dispenser 390 is used to dispense a liquid epoxy material 400 into the well 380. The dispenser 390 may be a needle or a syringe in certain embodiments. In some embodiments, the epoxy material 400 has a viscosity in a range from about 1 cP to about 10,000 cP. As shown in FIG. 4, the epoxy material 400 is dispensed onto a sidewall 380A of the well 380. The difference in surface energies between the substrate 210 and the epoxy material 400 causes a capillary effect. Due to the capillary effect, the epoxy material 400 wicks down the sidewall 380A of the well 380, across the back surface of the transducer, and then up the other sidewall 380C of the well 380. The dispenser 390 dispenses the epoxy material 400 in this manner until the epoxy material almost completely fills the entire well 380.

In the illustrated embodiments, an operator can control the dispense pressure and dispense time. Dispense pressure is dependent on the epoxy viscosity and the size of the dispenser 390. A dispensing speed may or may not be measured, but it is dependent on the size of the well 380 and the dispensing pressure. Once a suitable pressure is found, dispense time is manipulated to control the amount of epoxy dispensed into the well 380. The placement (i.e. on the side of the well 380) of the dispenser and the amount of epoxy 400 dispensed thereinto are carefully controlled. A sufficient amount of epoxy 400 should be dispensed into the well 380 so that when the wafer is thinned later, the well 380 is full with epoxy. On the other hand, the amount of epoxy dispensed should not completely fill the well 380 prior to wafer thinning/back grinding, because the transducer film (discussed below) will not have anywhere to go when shaping pressure is applied to the face of it, which means the transducer film will not be capable of being shaped like a lens.

To induce or facilitate the capillary effect discussed above, some additional measures may be taken in various embodiments. For instance, a tip 390A of the dispenser 390 may be positioned sufficiently adjacent to the sidewall 380A. In some embodiments, the tip 390A of the dispenser 390 is in physical contact with the sidewall 380A. In other embodiments, the tip 390A and the sidewall 380A are positioned sufficiently close so that the epoxy 400 is guaranteed to make contact with the sidewall 380A when it exits the tip 390A. The distance (if any) between the tip 390A and the sidewall 380A may be a function of a plurality of factors, including (but not limited to) surface energy of the tip 390A, epoxy, sidewall and atmosphere (which is dependent on ambient temperature and relative humidity), as well as capillary number of the epoxy 400. In any case, the close proximity of the tip 390A of the dispenser and the sidewall 380A ensures that the dispensed epoxy material 400 will come into contact with the sidewall 380A first, rather than dripping down directly to a bottom 380B of the well (the bottom 380B of the well may be the exposed back side surface of the substrate 210, for example). In some embodiments, the vertical position of the tip 390A may also vary as the epoxy material 400 is dispensed. For example, the tip 390A may initially be positioned closer to the bottom 380B of the well 380. As the epoxy material 400 is being dispensed into the well 380, the tip 390A may be moved "up" away from the bottom 380B of the well, while still maintaining close proximity to the sidewall 380A.

Figure 5:
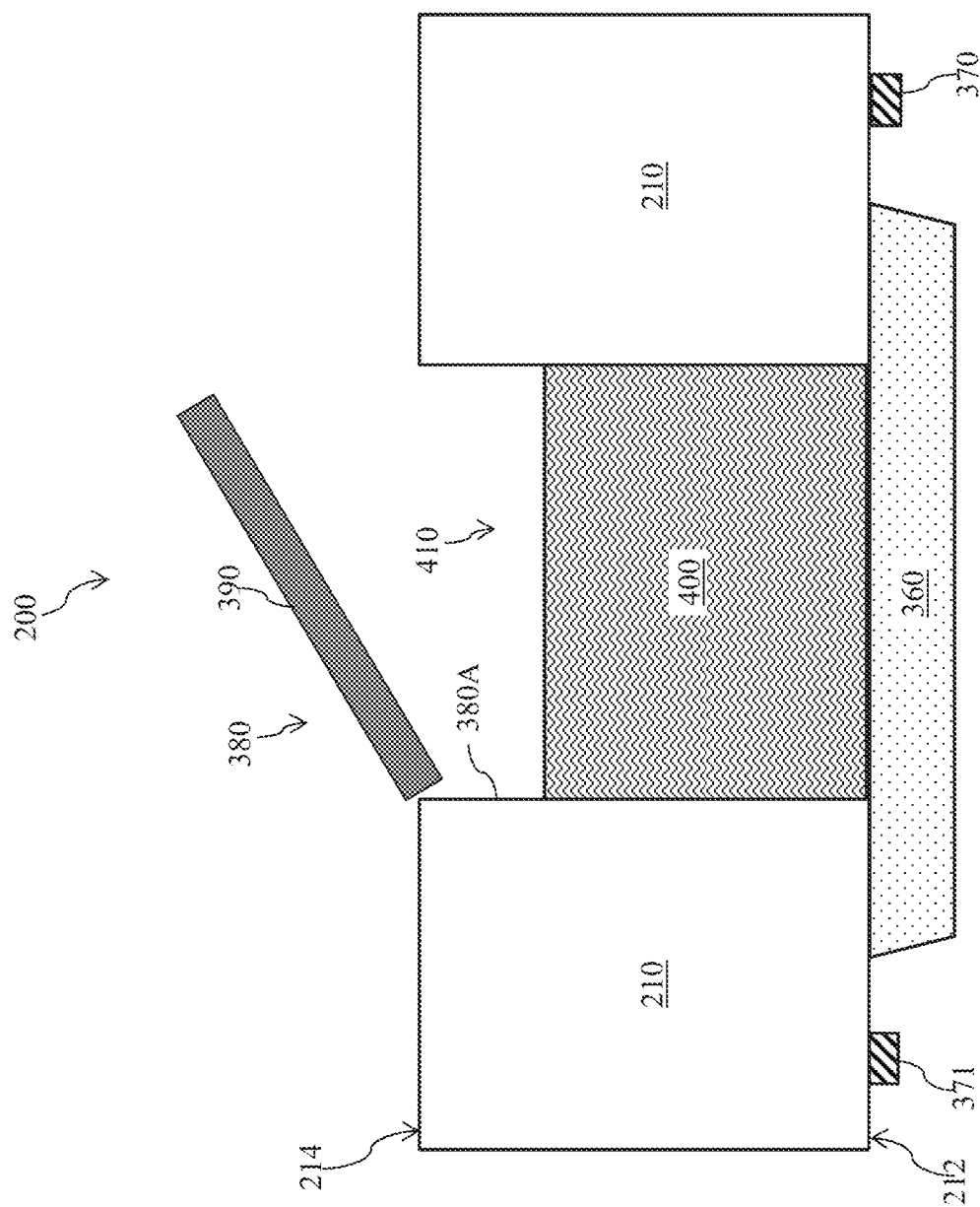

In some embodiments, the well 380 is not 100% filled. In order words, the dispenser 390 stops dispensing the epoxy 400 before the well 380 is 100% filled. This leaves some head space in the well 380, which reserves room for the transducer membrane 360 (FIG. 3) to be shaped back into the well 380. This scenario is graphically illustrated in FIG. 5, which is a simplified diagrammatic cross-sectional side view of the transducer 200. Once again, the transducer 200 is flipped upside-down from the view shown in FIG. 3. As shown in FIG. 5, the dispenser 390 is used to dispense the epoxy material 400 into the sidewall 380A of the well 380. The epoxy material 400 wicks down the sidewall 380A and gradually fills the well 380 due to the capillary effect discussed above. This process helps prevent air bubbles in the epoxy material as it is dispensed into the well 380.

The dispensing process ends while some head room or head space 410 in the well is maintained. The amount of head space 410 may be predetermined or predefined. In some embodiments, the amount of head space 410 is dependent on a diameter of the transducer 200 and the desired focal length of the device (which is correlated to an "F number"). For example, an equation $D=a/(8*F)$ can be used to determine the amount of deflection (D) (at the center position of the transducer membrane) needed for a given aperture (a) and a desired F number (F) (the F number=2×the focal length). As an example, an F number of about 3 mm is desired (i.e., focal length=1.5 mm), and the transducer aperture diameter is about 0.5 millimeters (mm). To achieve such F number and the transducer aperture diameter, the deflection (D) is calculated to be about 0.019 mm. In other words, the transducer membrane 360 needs to be deflected by about 0.019 mm. It is also understood that some additional head room may be allowed to account for manufacturing tolerances. Of course, it is understood that these numbers here are provided merely as examples, and that other numerical values may be used in alternative embodiments.

Figure 6:
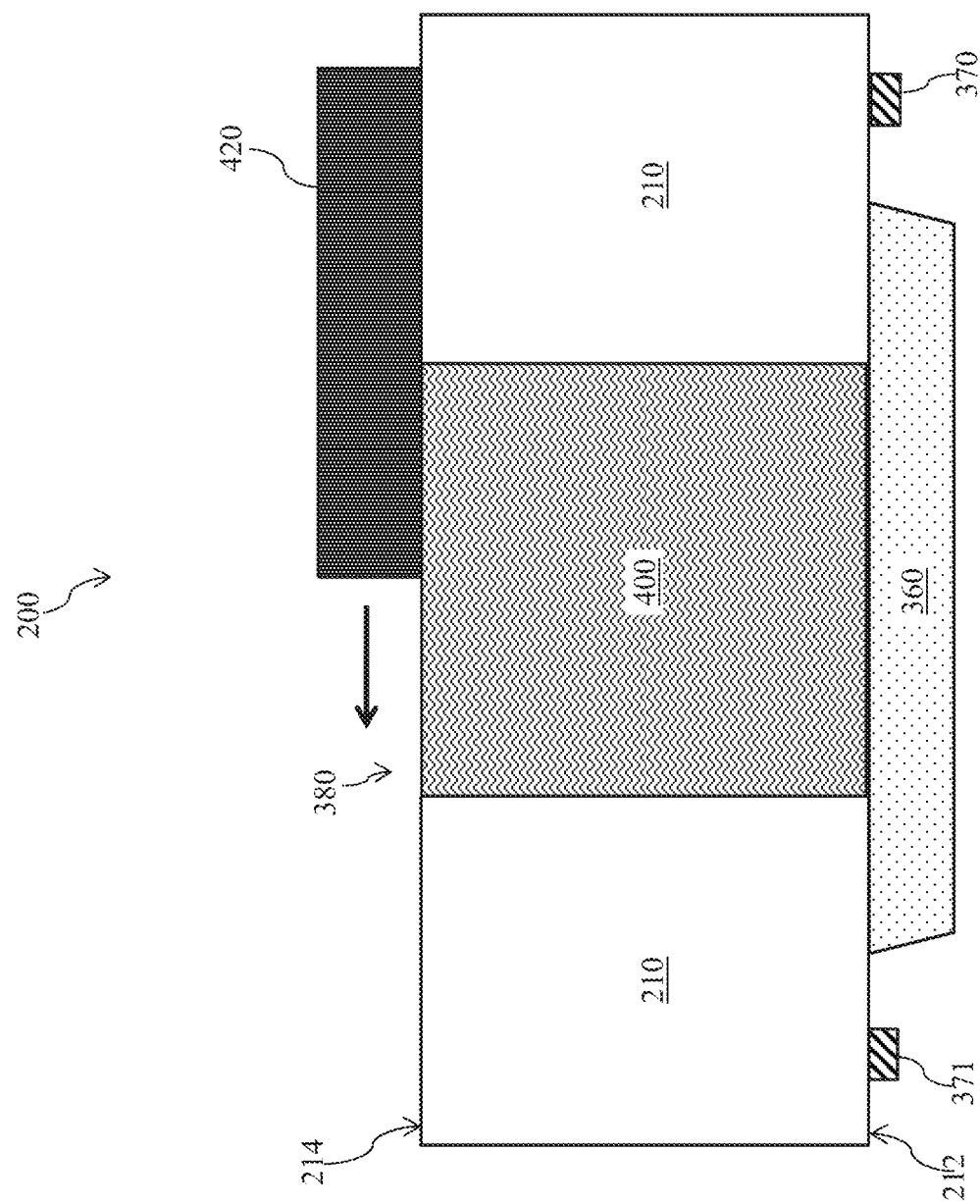

In alternative embodiments, the well 380 may be completely filled with the epoxy material 400, which may be intentional or inadvertent. In that case, a squeegeeing process is performed to remove undesired excess epoxy material off the back side 214 of the substrate 210. The squeegeeing process is shown in FIG. 6, which is a simplified diagrammatic cross-sectional side view of the transducer 200. As shown in FIG. 6, the well 380 is completely filled by the epoxy material 400. This may be undesirable because now there is no room to account for the (upcoming) deflection of the transducer membrane 360. Therefore, a squeegeeing device 420 is placed on the surface 214 of the substrate 210. The squeegeeing device 420 moves along the surface 214 of the substrate. As it passes by the epoxy material 400 in the well 380, it also creates a capillary effect. Due to the capillary effect, some of the epoxy material 400 is pulled out of the well 400. As such, undesired excess epoxy material 400 may still be removed from the well 380, thereby creating the head room 410 shown in FIG. 5. As discussed above, the amount of the head room 380 is configured to be enough to account for the deflection of the transducer membrane 360, which will be discussed below in more detail.

Figure 7:
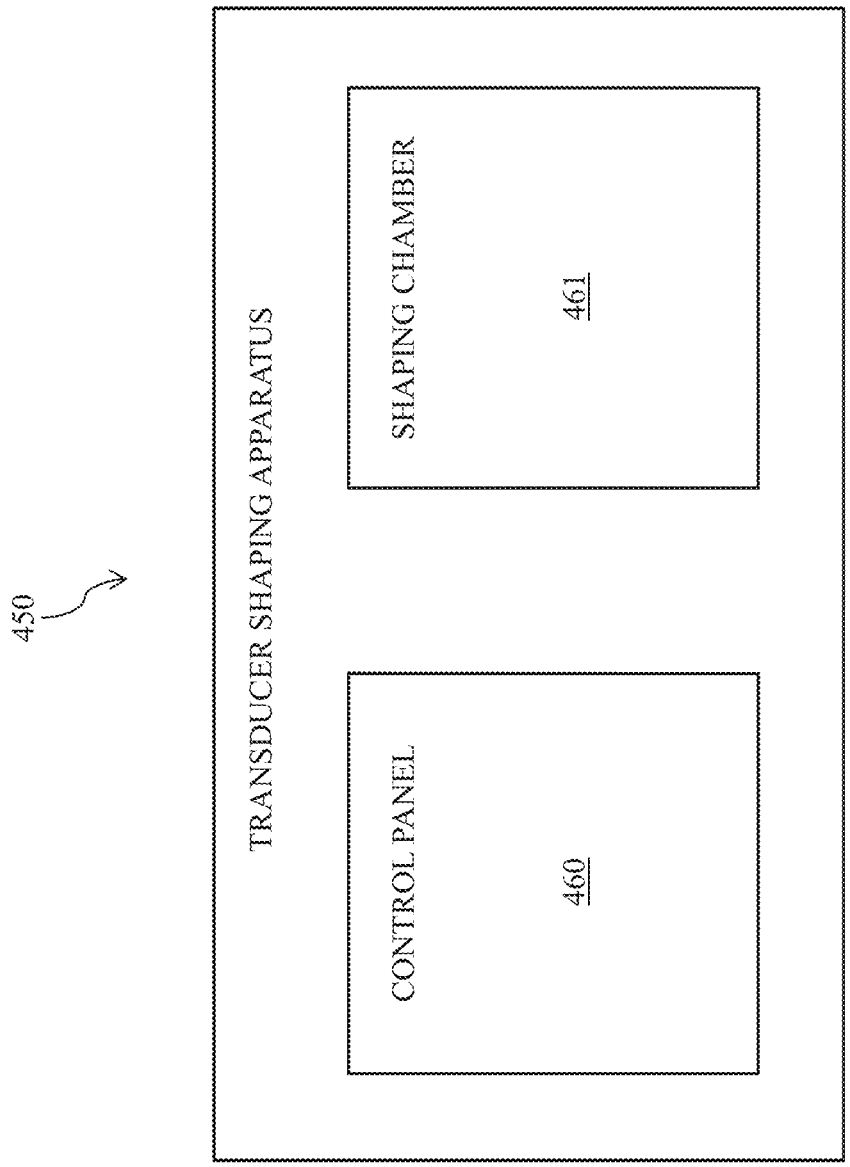
Figure 8:
Figure 9:
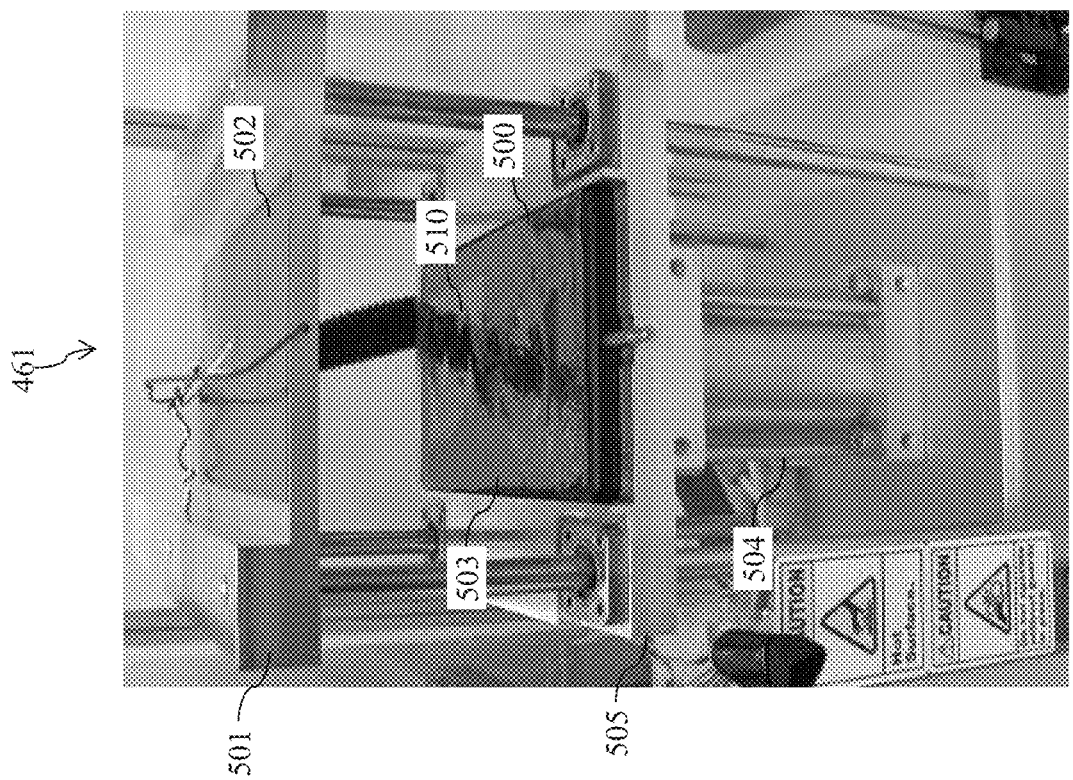

According to the various aspects of the present disclosure, the transducer 200 is shaped using a transducer shaping apparatus 450, an embodiment of which is shown in the simplified block diagram of FIG. 7. The transducer shaping apparatus 450 is an automated piece of equipment in the present disclosure, which acts like an internally pressurized heated metal press. The transducer shaping apparatus 450 includes a control panel 460 and a shaping chamber 461 that is communicatively coupled with the control panel 460. The control panel 460 includes various control and input/output mechanisms to facilitate interaction with a human user. The shaping chamber 461 includes various mechanical and electrical components to carry out the actual shaping of the transducer membrane 360 in response to instructions received from the control panel 460. Diagrammatic perspective views of the control panel 460 and the shaping chamber 461 are shown in FIGS. 8 and 9, respectively. The deflection operation of the transducer membrane 360 is discussed below in view of FIGS. 8-9 in more detail.

Referring to FIG. 8, the control panel 460 allows an operator to set process parameters including: cure temperature, shaping pressure, process time, and chamber closing pressure. The control panel 460 also allows the operator to start and stop the process via a "Start" button 470, and a "Stop/Reset" button 471. The control panel 460 also includes the following interactive mechanisms: a mechanism 472 for setting and displaying remaining process time, a mechanism 473 for setting and displaying cure temperature, a mechanism 474 for setting and displaying current shaping pressure, a mechanism 475 for setting and displaying current closing pressure, a mechanism 476 for setting and displaying current voltage applied to the shaping pressure regulator, and a mechanism 477 for setting and displaying current voltage applied to the closing pressure regulator. The control panel 460 also includes a pressure adjust mechanism 478 for adjusting pressure. In addition, the control panel 460 has a process indicator button 479 for indicating a process is ongoing, and an alarm indicator button 480 for alerting the operator there is an alarm. In certain embodiments, the regulator responds to voltage applied from 1-5 Volts (DC) in a linear manner. One or more 0-100 PSI regulators are also used. Therefore, 1 Volt corresponds to 20 PSI, 2 Volts corresponds to 40 PSI, 3 Volts corresponds to 60 PSI, etc. Resolution on the voltage indicator is 0.001 volt so as to allow for fine pressure tuning.

Although not illustrated, a digital relay is implemented inside the control panel 460. The digital relay controls process sequence by sending output pulses to a timer (e.g., the mechanism 472), and air pressure solenoids (inside the instrument enclosure and not visible in FIG. 8), and receiving inputs from the timer, the start and stop switches 470-471, and a switch mounted on the backing plate (shown in FIG. 9 and discussed below) of the shaping chamber 461. When this switch is closed, it indicates that the shaping chamber 461 is closed.

Referring now to FIG. 9, the shaping chamber 461 includes a removable part carrier 500. The part carrier 500 may have a specific geometry machined into it for the transducer profiles being shaped. For example, in some embodiments, the part carrier 500 accommodates one or more 1"×1" coupons of transducers (also referred to as a transducer coupon). Each transducer coupon has a plurality of transducers on it, for example 144 transducers. Since the part carrier 500 carries transducer coupons, the part carrier 500 may also be referred to as a transducer coupon carrier. In some embodiments, the transducer 200 may be placed on the part carrier 500 before the epoxy material 400 is dispensed into the well 380. This may take place when the part carrier 500 is outside the shaping chamber 461. After the epoxy fill process is completed (and squeegeeing if that is needed), the part carrier 500 and the transducer 200 placed thereon are then transported into the shaping chamber 461.

The shaping chamber 461 includes a backing plate 501. The backing plate 501 supports the well/epoxy side of the substrate 210 when under pressure. The backing plate 501 also houses a heating element 502 and conducts heat from the heating element 502 to the epoxy material 400 and the substrate 210 of the transducer 200. In some embodiments, the backing plate 501 is made of a thermally conductive metal material, for example aluminum. To prevent undesired adhesion between the transducer 200 and the backing plate 501 (especially as the epoxy material 400 cures), the present disclosure utilizes a release agent 503 (or release film). In some embodiments, the release agent 503 includes a thin fluoropolymer release film between the backing plate 501 and the substrate 210 of the transducer 200. The film may be as thin as 0.001 inches to 0.003 inches, for example. In other embodiments, the backing plate 501 is anodized with a polytetrafluoroethylene (PTFE) agent to facilitate the release. Of course, other fluoropolymer films such as FEP or PFA may be used as suitable release agents as well. The use of liquid agents may not be appropriate, as they are likely to transfer to the substrate 210 and cause contamination of the transducer 200, which would inhibit other downstream processes.

The shaping chamber 461 also includes an air cylinder 504 and a bottom plate 505 resting on the air cylinder 504. The air cylinder 504 pushes the bottom plate 505 up against the backing plate 501. When a part carrier (for example the part carrier 500) is loaded into the bottom plate 505, O-rings on the bottom plate seal against the part carrier once the air cylinder closes the chamber. When a part 510 (e.g., the transducer device 200) is loaded into the part carrier 500, the part 510 seals against a gasket in the part carrier 500 when the air cylinder 504 closes the chamber. Once the chamber closes, and the part 510, the part carrier 500, and the bottom plate 505 are sealed against one another, a solenoid (not illustrated in FIG. 9) in the control panel 460 (FIGS. 7-8) opens and pressurizes the shaping chamber. The rods and linear bearing help guide the bottom plate 505 as it travels vertically. In some embodiments, flow restrictors are implemented in the plumbing lines to control the rate at which the air cylinder closes the chamber and the rate at which the shaping chamber pressurizes.

In the present case, after the epoxy 400 has been dispensed into the well 380 of the transducer 200, the transducer 200 is loaded as the part 510 into the shaping chamber 461. Using the control panel 460, the operator can set the various process parameters and start the process of shaping the transducer membrane 360. As the shaping chamber 461 closes and seals, an air pressure is applied to the front side 212 of the transducer 200. The air pressure forces the transducer membrane 360 into a concave shape. In some embodiments, heat is applied to the back side 214 of the transducer 200 while the transducer membrane is being deflected. The heat cures the epoxy material 400 (or expedites the curing of the epoxy) filling the well 380. The cured epoxy material 400 serves to hold the shaped transducer membrane 360 into place. It some alternative embodiments, the epoxy material 400 may be cured by heat after the transducer membrane 360 has already achieved the arcuate shape through deflection. In other words, air pressure may continue to be applied to the transducer membrane 360, so that it will hold its arcuate shape, while the heat is applied to the epoxy material 400.

The epoxy material 400 also serves to deaden sound coming off the back of the transducer. In order to do so, the backing material 400 contains an acoustically attenuative material so that it can absorb acoustic energy (in other words, sound waves) generated by the transducer membrane 360 that travels (propagates) into the ultrasound transducer 200 (for example, from the transducer membrane 360 into the backing material 400). Such acoustic energy includes acoustic energy that is reflected from structures and interfaces of a transducer assembly, for example when the ultrasound transducer 200 is included in the transducer assembly 122 of FIG. 1. To adequately deaden the sound waves, the backing material 400 may have an acoustic impedance greater than about 4.5 mega-Rayls in some embodiments.

FIG. 10 is a diagrammatic perspective view of a portion of the shaping chamber 461A in more detail. The bottom plate 505 is shown as being empty—no part carrier 500 is placed on the bottom plate 505. The air cylinder 504 still provides support for the bottom plate 505. A plurality of air inlets 520 are dispersed throughout the bottom plate 505. These air inlets 520 each include a sealing O-ring. The air inlets 520 are also coupled to air inlet tubing 530. The tubing 530 is coupled to the air cylinder 504 to open/close the cylinder 504. Other tubing is coupled to the bottom plate 505 and moved through the bottom plate 505, through the part carrier (not illustrated in FIG. 10), and against the face of the transducer coupon. The tubing 530 feeds to the hole inside the air inlet 520, and the part carrier would have a corresponding hole. The part carrier would seal against the air inlets 520.

Figure 11B:
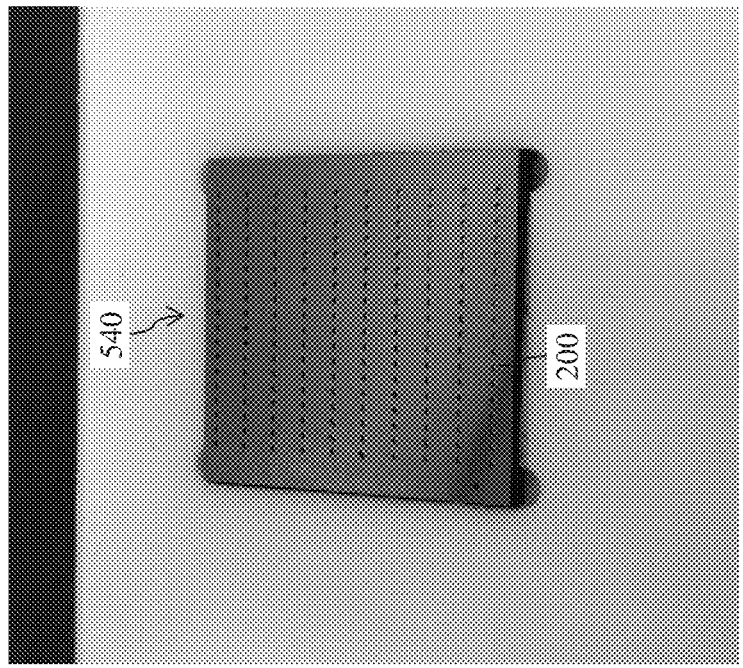
Figure 11A:
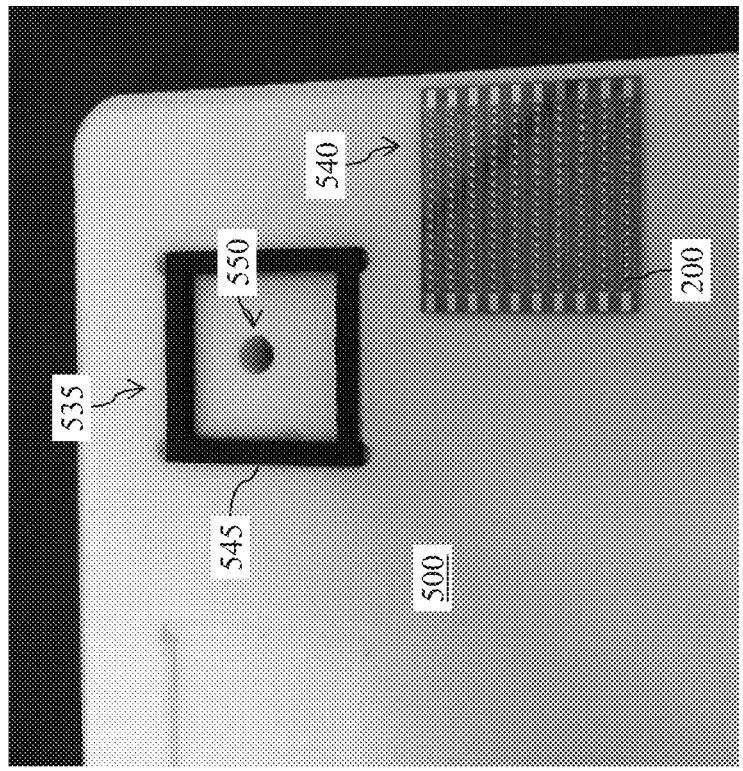

FIG. 11A illustrates a diagrammatic top view of the removable part carrier 500. The part carrier 500 includes one or more concave slots 535, one of which is shown as an example in FIG. 11A. Each slot 535 is geometrically configured to accommodate a transducer coupon, an example one of which is shown in FIGS. 11A and 11B and labeled with the reference numeral 540. As discussed above, the transducer coupon 540 is made from a part of the wafer on which a plurality of the transducers 200 are fabricated. Before the transducer membrane shaping step, the wafer is sliced or diced into a plurality of transducer coupons 540. Each transducer coupon 540 includes a plurality of transducers 200, for example 144 transducers, which are arranged in rows and columns as shown in FIGS. 11A and 11B. It is understood that FIG. 11A shows a front side view (i.e., the side 212 in FIGS. 2-3 and 5-6) of the transducers 200, whereas FIG. 11B shows a back side view (i.e., the side 214 in FIGS. 2-3 and 5-6) of the transducers 200. In other words, FIG. 11 shows the transducer membranes 360 being exposed, whereas FIG. 11B shows the epoxy 400 partially filling the wells 380. In the illustrated embodiments, the slot 535 on the part carrier 500 has a substantially square shape, since that is the shape of the transducer coupon 540. However, it is understood that the slot 535 and the transducer coupon 540 may be shaped differently in alternative embodiments, as long as the slot 535 is geometrically shaped to accommodate the transducer coupon 540.

To enhance the sealing performance when the transducer membranes 360 are being shaped, the present disclosure utilizes a gasket 545 in each slot 535 of the part carrier 500. The gasket 545 is a "ring-like" device but has four sides as in a square. This is because the gasket 545 also is shaped to accommodate with the shape of the transducer coupon 540. In operation. one side of the gasket 545 presses upon the surface of the part carrier 500 inside the slot 535, and the other side (opposite side) of the gasket 545 presses upon the transducer coupon 540. In other words, the front side 212 of the transducer coupon 540 will not make actual contact with the surface of the part carrier 500, as the gasket acts as an intermediary or a buffering mechanism between the part carrier 500 and the transducer coupon 540. This arrangement allows better sealing of the transducer coupon 540 during the transducer membrane shaping process.

The part carrier 500 also has a plurality of air lets 550, one in each of the slots 535. During the transducer membrane shaping process, air pressure may be applied to the transducer membranes 360 through the air inlet 550. The air pressure deflects the transducer membranes 360 for all the transducers 200 on the transducer coupon 540, which is a much more efficient way of manufacture than conventional methods where transducer membranes are deflected one at a time.

Figure 12B:
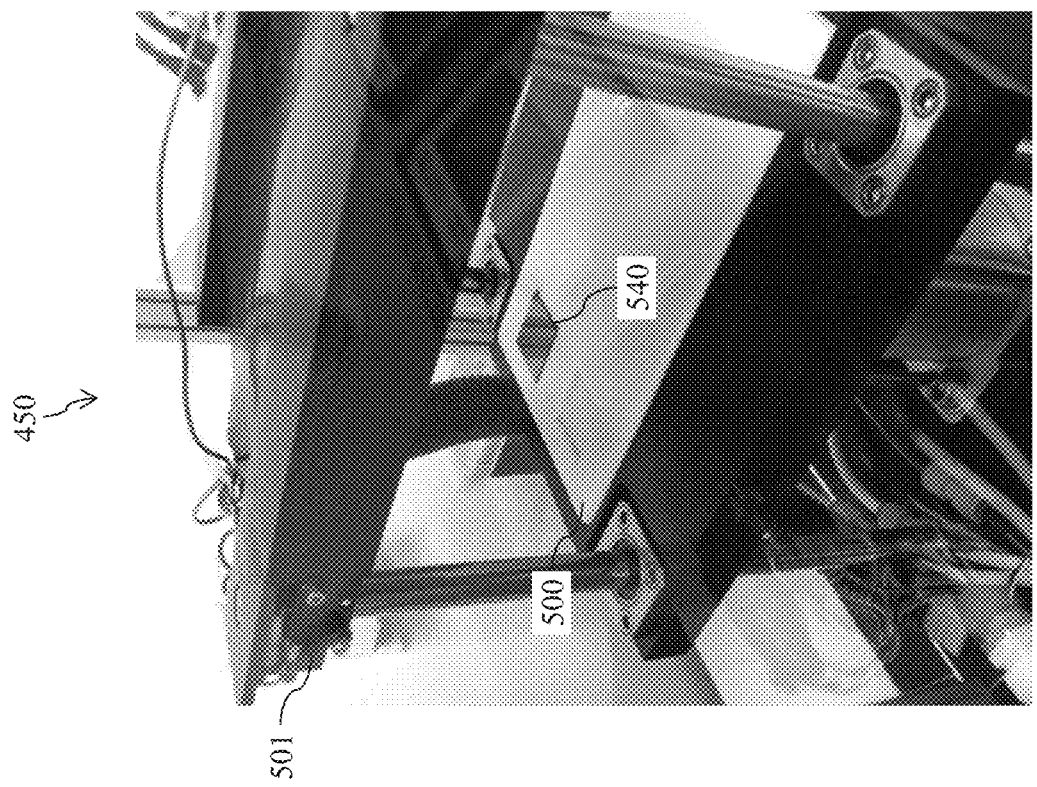
Figure 12A:
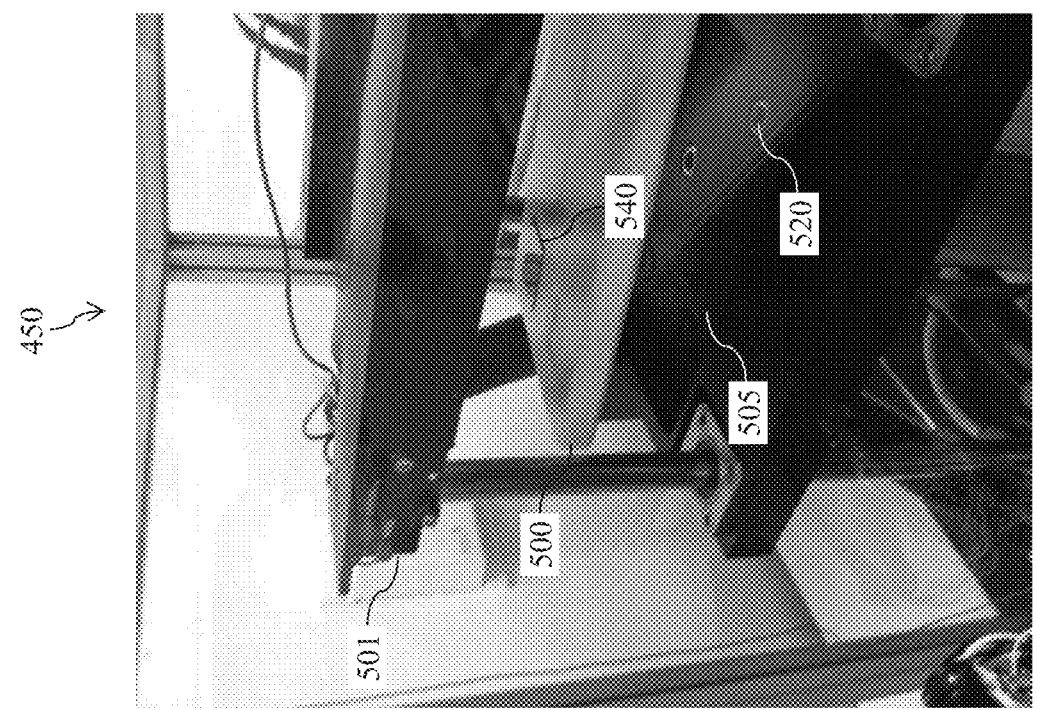

FIGS. 12A and 12B are diagrammatic perspective views of a portion of the transducer shaping chamber 461. Specifically, FIGS. 12A and 12B illustrate the backing plate 501 (also referred to as top plate), the removable part carrier 500 having a transducer coupon 540 located therein, and the bottom plate 505. As is shown in FIGS. 12A and 12B, the part carrier 500 is disposed in between the backing plate 501 (i.e., the top plate) and the bottom plate 505. In the embodiments of the present disclosure, the part carrier 500 is placed on the bottom plate 505, which is a concave slot that is geometrically shaped to accommodate the part carrier 500. The bottom plate 505 and the backing plate 501 can be moved towards each other to create a sealing chamber, inside which the transducer coupon 540 may be shaped by application of air pressure. The air pressure may be applied through the air inlets 520 (also referred to as O-rings) on the bottom plate 505. The air inlets 520 are coupled to the air inlets 550 on the part carrier 500.

To provide more clarity to the transducer membrane shaping operation discussed above, FIG. 13 is provided, which illustrates a diagrammatic cross-sectional view of a portion of the transducer shaping chamber 461 during the transducer membrane shaping operation. As is shown in FIG. 13, a transducer coupon 540 is sealed between the backing plate 501 (i.e., top plate) and the gasket 545. The transducer coupon 540 and the gasket 545 are each placed inside the square-shaped slot of the part carrier 500. The part carrier 500 is also sealed between the bottom plate 505 and the backing plate 501. The air inlet 520 (shown in FIGS. 12A-12B) extending vertically through the bottom plate 505 is communicatively coupled with the air inlet 550 (shown in FIGS. 11A-11B) extending vertically through the part carrier 500. Thus, pressurized air may be applied against the transducer membranes on the transducer coupon 540 through the air inlets 520 and 550. It is understood that the gasket 545 does not block the air flow. The cross-sectional view of the gasket 545 shows one of the four "sides" or edges of the gasket 545, but an empty space is surrounded or encircled by these four sides. It is through such empty space that pressurized air from the inlets 520 and 550 reaches the transducer membranes on the transducer coupon 540.

In accordance with certain embodiments of the present disclosure, an internal plumbing mechanism (e.g., air tubes) 560 may be implemented within the part carrier 500. The plumbing mechanism 560 extends horizontally through the part carrier 500 and is also communicatively coupled with the air inlet 550 (that extends vertically through the part carrier 500). In doing so, the plumbing mechanism 560 can deliver pressurized air to adjacent air inlets (not illustrated in FIG. 13). In other words, the structural arrangement of the portion of the transducer shaping chamber 461 shown in FIG. 13 may be repeated a number of times. These additional transducer coupons 540 may be placed in the other slots of the part carrier 500, for example, and are also sealed against the backing plate 501 through their respective gaskets 545. Air may be delivered to these other transducer coupons 540 through the plumbing mechanism 560, which couples together two or more of the air inlets 550 each aimed at a different one of the transducer coupons 540. One benefit of applying pressurized air in this manner is that more uniformed air pressure can be applied to different groups of transducer coupons 540 at the same time, which may lead to more uniformity of the deflection of the transducer membranes. Another benefit of the transducer shaping chamber 461 is that the backing plate 501 may be heated, which expedites the curing of the epoxy material in the wells.

Figure 14:
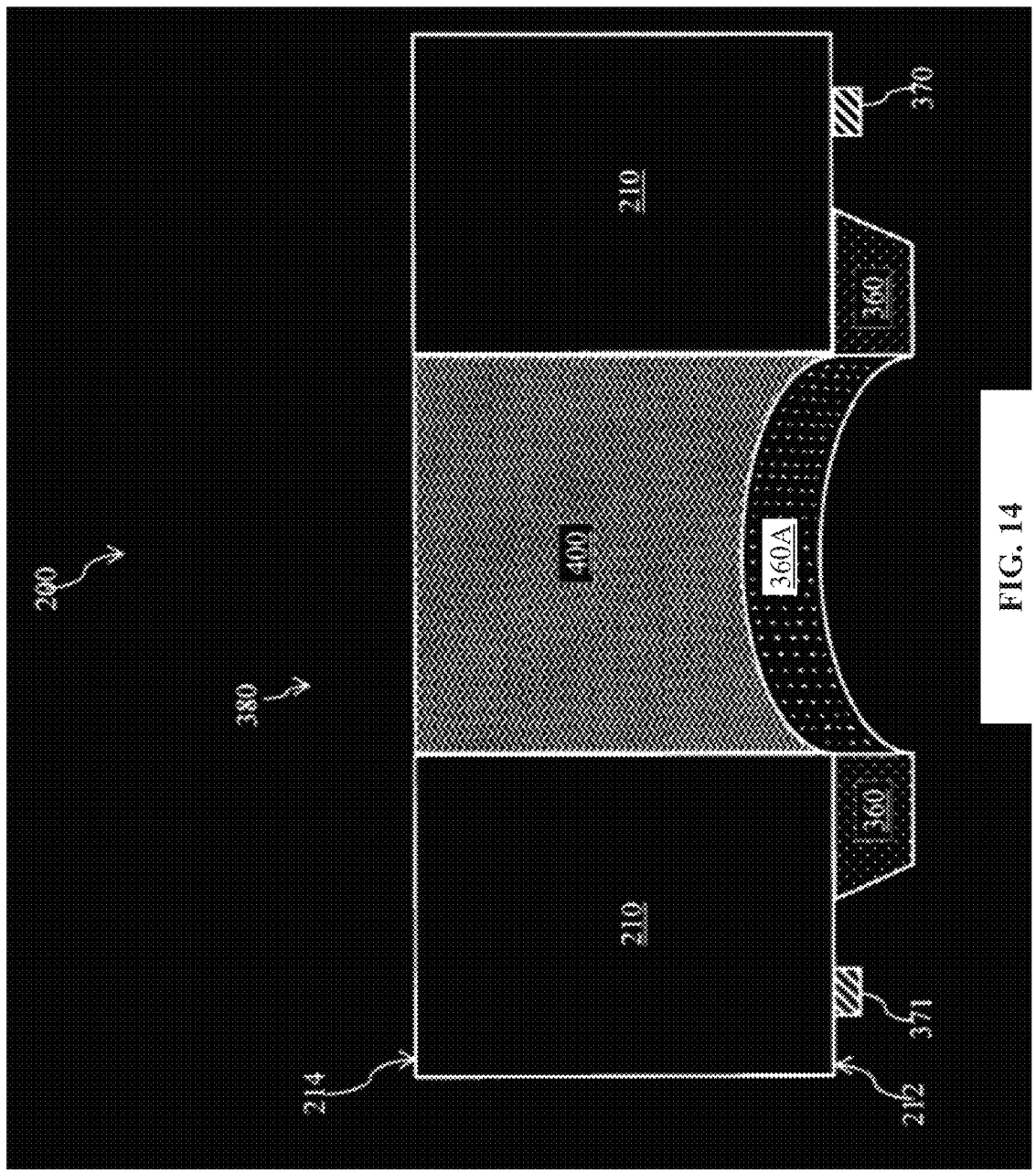

FIG. 14 is a diagrammatic cross-sectional side view of the transducer 200 after the transducer membrane 360 has been deflected by the transducer shaping apparatus 450 discussed above. It is understood that the side 214 (i.e., the back side) of the substrate 210 has already been thinned at this point. In other words, a suitable grinding or polishing process may be performed to planarize the back side of the substrate 210 after the transducer membrane 360 has been shaped. Any excess epoxy material 400 outside the well 380 will be removed during this thinning process, so that the epoxy material 400 will be substantially co-planar with (or below) the back side of the substrate 210. The thinning process is performed outside the transducer shaping apparatus and with a different machine, As shown in FIG. 14, a portion 360A of the transducer membrane is defected by the air pressure from the shaping chamber 461 such that it has an arcuate shape. The arcuate shape of the transducer membrane 360 helps is spherically focus ultrasound signals emitted therefrom. Of course, it is understood that the transducer shaping apparatus 450 may shape the transducer membrane 360 to have other shaping configurations in different embodiments, so as to achieve various other focusing characteristics. For example, in an alternative embodiment, the transducer membrane 360 may have a more arcuate shape (than it does in the embodiment shown in FIG. 14) or a more planar shape.

FIG. 15 is a flowchart of a method 600 for fabricating an ultrasound transducer according to various aspects of the present disclosure. The method 600 includes a step 610, wherein a substrate is provided. The substrate has a first side and a second side opposite the first side. In some embodiments, the substrate is a silicon substrate and may contain microelectronic circuitry therein.

The method 600 includes a step 620, in which a transducer membrane is formed over the first side of the substrate. The transducer membrane includes a piezoelectric component.

The method 600 includes a step 630, in which a well is formed in the substrate from the second side.

The method 600 includes a step 640, in which a backing material is dispensed into the well to induce a capillary effect. In more detail, the backing material is dispensed onto a first sidewall of the well. Due to the capillary effect caused by the surface energy difference between the sidewall of the well and the backing material, the backing material wicks down the sidewall, across the back side of the substrate exposed by the well, and up a second sidewall of the well. In some embodiments, the backing material is an epoxy material.

In some embodiments, the step 640 is performed so that the well is free of being completely filled by the backing material. In some embodiments, the step 640 is performed so that the well is completely filled by the backing material. In that case, the method 600 may further include a step of performing a squeegeeing process to the second side of the substrate so as to remove excess backing material from the well through another capillary effect.

The method 600 includes a step 650, in which the transducer membrane is deflected so that the transducer membrane has a concave shape. In some embodiments, the step 650 includes applying air pressure towards the transducer membrane so that a portion of the transducer membrane is deflected into the well. In some embodiments, the step 650 is performed at least in part using a transducer shaping chamber. The pressurizing, opening, and closing of the transducer shaping chamber are each performed in an automated manner.

The method 600 includes a step 660, in which the backing material is cured while the deflection of the transducer membrane is maintained. The backing material may be cured by heat. In some embodiments, the transducer shaping chamber includes a backing plate configured to support the second side of the substrate while the transducer membrane is deflected. The backing plate may include one or more heating elements configured to generate heat, so that the backing material in the well may be heated during the deflecting of the transducer membrane. The heating of the backing material helps expedite the curing of the backing material.

The method 600 may further include a step of applying a release agent to the backing plate to prevent adhesion between the backing material and the backing plate. In some embodiments, the applying the release agent includes anodizing the backing plate with a polytetrafluoroethylene (PTFE) material. In other embodiments, the applying the release agent includes applying a fluoropolymer release film between the backing material and the backing plate.

It is understood that additional fabrication steps may be performed to complete the fabrication of the transducer. However, these additional fabrication steps are not discussed herein for reasons of simplicity.

Based on the above discussions, it can be seen that the transducer shaping according to the embodiments of the present disclosure offers numerous advantages over conventional methods. Of course, it is understood that not all advantages are necessarily discussed herein, other embodiments may offer different advantages, and no particular advantage is required for all embodiments.

As one example, the present disclosure involves heating the epoxy material to expedite the epoxy curing. As another example, the transducer well is filled using a capillary effect, which allows the epoxy material to wick down the side of the well, across the back side of the transducer face, and up the remaining side of the well. This filling process helps prevent air bubbles in the well. The present disclosure reserves sufficient head space on the back side of the epoxy material during the epoxy dispensation into the transducer well, so that there is enough room to allow for the deflection of the transducer membrane. In situations where the epoxy has filled the transducer well too much (i.e., not enough head space), a squeegeeing process may also be performed to the back side of the transducer substrate to induce a capillary effect, which will pull excess epoxy out of the well, thereby creating additional head space in the well.

As yet one more example of the advantages offered by the embodiments of the present disclosure, a release agent may be implemented between the transducer substrate and the backing plate of the transducer shaping chamber to prevent the epoxy from curing to the tool. As another example, the transducer shaping apparatus of the present disclosure is automated: the opening and closing of the shaping chamber is automated, as is the pressurizing of the shaping chamber. As one more example, flow restrictors may be used in the plumbing lines to control the rate at which the air cylinder closes the shaping chamber and the rate at which the shaping chamber pressurizes. As a further example, a removable part carrier that has a specific geometry machined into it is utilized to shape the transducer profile.

One aspect of the present disclosure involves a method of fabricating a miniature ultrasound transducer. The method includes: providing a substrate having a first side and a second side opposite the first side; forming a transducer membrane over the first side of the substrate, the transducer membrane including a piezoelectric component; forming a well in the substrate from the second side; dispensing a backing material onto a first sidewall of the well in a manner so as to create a capillary effect that causes the backing material to wick down the sidewall, across the back side of the substrate exposed by the well, and up a second sidewall of the well; and deflecting the transducer membrane so that the transducer membrane has a concave shape.

In some embodiments, the dispensing is performed so that the well is free of being completely filled by the backing material.

In some embodiments, the dispensing is performed so that the well is completely filled by the backing material, and further comprising: performing a squeegeeing process to the second side of the substrate so as to remove excess backing material from the well through another capillary effect.

In some embodiments, the backing material includes an epoxy material.

In some embodiments, the deflecting comprises applying air pressure towards the transducer membrane so that a portion of the transducer membrane is deflected into the well.

In some embodiments, the method further includes: heating the backing material during the deflecting of the transducer membrane to cure the backing material.

In some embodiments, the deflecting is performed at least in part using a transducer shaping chamber, and wherein pressurizing, opening, and closing of the transducer shaping chamber are each automated.

In some embodiments, the transducer shaping chamber includes a backing plate configured to support the second side of the substrate while the transducer membrane is deflected, and further comprising applying a release agent to the backing plate to prevent adhesion between the backing material and the backing plate.

In some embodiments, the applying the release agent comprises anodizing the backing plate with a polytetrafluoroethylene (PTFE) material.

In some embodiments, the applying the release agent comprises applying a fluoropolymer release film between the backing material and the backing plate.

Another aspect of the present disclosure involves a method of fabricating an ultrasound transducer. The method includes: providing a wafer having a first side and a second side opposite the first side; forming a transducer membrane over the first side of the wafer, the transducer membrane including a piezoelectric component; forming an opening in the wafer from the second side; partially filling the opening with an epoxy material in a manner such that a predetermined amount of head space is reserved in the well; applying air pressure to the transducer membrane from the first side to deflect a portion of the transducer membrane towards the second side; and curing the epoxy material by heat during the applying the air pressure.

In some embodiments, the partially filling the opening is performed by dispensing the epoxy material onto a first sidewall of the opening to induce a capillary effect that causes the epoxy material to wick down the sidewall, across the second side of the wafer exposed by the opening, and up a second sidewall of the opening.

In some embodiments, the deflecting is performed such that the transducer membrane achieves an arcuate shape.

In some embodiments, the applying and the curing are performed at least in part using a transducer shaping chamber.

In some embodiments, the transducer shaping chamber is configured to pressurize, open, and close in an automated manner.

In some embodiments, the transducer shaping chamber includes a backing plate configured to support the second side of the wafer during the applying, wherein the backing plate includes heating elements configured to provide heat to the epoxy material during the curing.

In some embodiments, the method further includes: applying an adhesion-preventing fluoropolymer release film on the backing plate before the applying the air pressure.

In some embodiments, the backing plate is anodized with a polytetrafluoroethylene (PTFE) material.

Another aspect of the present disclosure involves a method of shaping a transducer. The method includes: providing a wafer having a first side and a second side opposite the first side; forming a multi-layered transducer membrane over the first side of the wafer, one of the layers of the transducer membrane being a piezoelectric layer; forming a well in the wafer, the well being open to the second side; dispensing an epoxy material into a sidewall of the well in a manner so as to induce a capillary effect that causes the well to be partially filled substantially without air bubbles; deflecting the transducer membrane by applying pressurized air from the first side until the transducer membrane achieves an arcuate shape; and curing the epoxy material while the transducer membrane is deflected.

In some embodiments, the deflecting and the curing are performed inside a transducer shaping apparatus.

In some embodiments, the method further includes thinning the wafer from the second side after the curing of the epoxy material.

In some embodiments, the dispensing is performed such that a predetermined amount of headspace is reserved in the well.

Yet another aspect of the present disclosure involves a transducer shaping chamber for shaping ultrasound transducers. The transducer shaping chamber includes: a transducer coupon carrier having one or more slots, the one or more slots each being geometrically shaped to hold a transducer coupon having a plurality of ultrasound transducers formed thereon; a first plate disposed over a first side of the transducer coupon carrier; and a second plate disposed over a second side of the transducer coupon carrier, the second side being opposite the first side; wherein the transducer shaping chamber is configured to move the first plate and the second plate toward each other so as to push against the transducer coupon carrier from the first and second sides, respectively, until the transducer coupon carrier has been sealed against the first plate and with the second plate.

In some embodiments, the transducer coupon carrier is detachable from the transducer shaping chamber.

In some embodiments, the transducers each have a transducer membrane disposed over a transducer well partially filled with epoxy.

In some embodiments, the transducer coupon carrier includes an air inlet facing the transducer coupon, the air inlet allowing air to be delivered collectively to the transducer membranes.

In some embodiments, the transducer shaping chamber is configured to deliver air to the transducer membranes so as to deflect each of the transducer membranes into an arcuate shape.

In some embodiments, the transducer shaping chamber is configured to heat up the first plate while the air is delivered, wherein the heated first plate expedites a curing of the epoxy partially filling the transducer well.

In some embodiments, the second plate includes an air hole communicatively coupled to the air inlet and through which the air is delivered to the transducer shaping chamber.

In some embodiments, the transducer coupon carrier includes an internal plumbing mechanism intersecting with, and communicatively coupled to, the air inlet, the internal plumbing mechanism being configured to allow air flow therein.

In some embodiments, the transducer shaping chamber further includes one or more gaskets disposed at least partially inside the one or more slots of the transducer coupon carrier, the one or more gaskets being configured to facilitate the sealing of the transducer coupon with the first plate.

Another aspect of the present disclosure involves a system for fabricating an ultrasound transducer. The system includes: a control panel that includes a plurality of control mechanisms configured to set a plurality of fabrication process parameters, the fabrication process parameters being selected from the group consisting of: process pressure, process time, process duration, and process voltage; and a transducer shaping chamber communicatively coupled to the control panel and configured to implement the fabrication process parameters therein in response to instructions from the control panel, the transducer shaping chamber including: a removable part carrier configured to load a transducer coupon having a plurality of transducers formed thereon, the transducers each having a transducer membrane disposed over a well partially filled with an epoxy; a first plate configured to support and seal against the part carrier from a first side, the first plate facing the transducer well; and a second plate configured to support and seal against the part carrier from a second side opposite the first side, the second plate facing toward the transducer membrane; wherein: the first and second plates are configured to be moved toward each other until the part carrier is sealed between the first plate and the second plate; and the transducer shaping chamber is configured to deflect the transducer membrane into an arcuate shape through application of pressurized air.

In some embodiments, the first plate is configured to be thermally heated.

In some embodiments, the transducer shaping chamber, in response to the fabrication process parameters set by the control panel, heats the first plate while delivering pressurized air to the transducers on the transducer coupon.

In some embodiments, the removable part carrier includes a plurality of slots, and wherein each slot is geometrically configured to hold a respective transducer coupon therein.

In some embodiments, the transducer shaping chamber further comprises a plurality of gaskets, and wherein each gasket is geometrically configured to be placed into a respective one of the slots.

In some embodiments, for each gasket, one side of the gasket is configured to seal against the removable part carrier, and an opposite side of the gasket is configured to seal against the transducer coupon.

In some embodiments, each slot of the removable part carrier includes an air inlet configured to receive the pressurized air.

In some embodiments, the second plate includes an air hole that is coupled to the air inlet of the removable part carrier.

In some embodiments, the removable part carrier includes an internal plumbing mechanism that is coupled to the air inlet in one or more of the slots.

Yet another aspect of the present disclosure involves a transducer shaping apparatus for shaping a plurality of ultrasound transducers collectively. The apparatus includes: a bottom plate having an air hole that allows a pressurized air to be delivered into the transducer shaping apparatus; a removable transducer coupon carrier disposed over the bottom plate, the transducer coupon carrier including a slot that is geometrically configured to hold and support a transducer coupon having a plurality of ultrasound transducers formed thereon, and wherein the slot includes an air inlet coupled to the air hole of the bottom plate, the air inlet allowing the pressurized air to be applied to the plurality of transducers collectively; a top plate disposed over the transducer coupon carrier, the top plate being configured to be heated; and wherein the top plate and the bottom plate are configured to be moved toward each other so as to seal against the transducer coupon carrier from opposites sides and seal the transducer coupon carrier therebetween while the pressurized air is applied to the plurality of transducers.

In some embodiments, the transducers each have a transducer membrane disposed over a transducer well at least partially filled with a backing material, and wherein the pressurized air applied to the transducer membranes causes each transducer membranes to be deflected into an arcuate shape.

In some embodiments, the transducer shaping apparatus is configured to heat up the top plate to expedite a curing of the backing material while the transducer membranes are being deflected by the pressurized air.

In some embodiments, the transducer coupon carrier includes an internal plumbing mechanism intersecting with, and communicatively coupled to, the air inlet, and wherein the internal plumbing mechanism is configured to allow air flow therein.

In some embodiments, the transducer shaping apparatus further includes a gasket disposed at least partially inside the slot of the transducer coupon carrier, the gasket being configured to seal against the transducer coupon carrier and against the transducer coupon.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A method of fabricating a miniature ultrasound transducer, the method comprising:
providing a substrate having a first side and a second side opposite the first side;
forming a transducer membrane over the first side of the substrate, the transducer membrane including a piezoelectric component;
forming a well in the substrate from the second side;
dispensing, using a needle or syringe, a backing material onto a first sidewall of the well in a manner so as to create a capillary effect that causes the backing material to wick down the sidewall, across the back side of the transducer membrane exposed by the well, and up a second sidewall of the well; and
deflecting the transducer membrane so that the transducer membrane has a concave shape.

2. The method of claim 1, wherein the dispensing is performed so that the well is free of being completely filled by the backing material.

3. The method of claim 1, wherein the dispensing is performed so that the well is completely filled by the backing material, and further comprising: performing a squeegeeing process to the second side of the substrate so as to remove excess backing material from the well through another capillary effect.

4. The method of claim 1, wherein the backing material includes an epoxy material.

5. The method of claim 1, wherein the deflecting comprises applying air pressure towards the transducer membrane so that a portion of the transducer membrane is deflected into the well.

6. The method of claim 1, further comprising: heating the backing material during the deflecting of the transducer membrane to cure the backing material.

7. The method of claim 1, wherein the deflecting is performed at least in part using a transducer shaping chamber, and wherein pressurizing, opening, and closing of the transducer shaping chamber are each automated.

8. The method of claim 7, wherein the transducer shaping chamber includes a backing plate configured to support the second side of the substrate while the transducer membrane is deflected, and further comprising applying a release agent to the backing plate to prevent adhesion between the backing material and the backing plate.

9. The method of claim 8, wherein the applying the release agent comprises applying a fluoropolymer release film between the backing material and the backing plate.

10. A method of fabricating an ultrasound transducer, the method comprising:
providing a wafer having a first side and a second side opposite the first side;
forming a transducer membrane over the first side of the wafer, the transducer membrane including a piezoelectric component;
forming an opening in the wafer from the second side;
partially filling the opening with an epoxy material in a manner such that a predetermined amount of head space is reserved in the well, wherein the partially filling the opening is performed by dispensing the epoxy material onto a first sidewall of the opening to induce a capillary effect that causes the epoxy material to wick down the sidewall, across the second side of the wafer exposed by the opening, and up a second sidewall of the opening;
applying air pressure to the transducer membrane from the first side to deflect a portion of the transducer membrane towards the second side; and
curing the epoxy material by heat during the applying the air pressure.

11. The method of claim 10, wherein the deflecting is performed such that the transducer membrane achieves an arcuate shape.

12. The method of claim 10, wherein the applying and the curing are performed at least in part using a transducer shaping chamber.

13. The method of claim 12, wherein the transducer shaping chamber is configured to pressurize, open, and close in an automated manner.

14. The method of claim 12, wherein the transducer shaping chamber includes a backing plate configured to support the second side of the wafer during the applying, wherein the backing plate includes heating elements configured to provide heat to the epoxy material during the curing.

15. The method of claim 14, further comprising: applying an adhesion-preventing fluoropolymer release film on the backing plate before the applying the air pressure.

16. A method of shaping a transducer, comprising:
providing a wafer having a first side and a second side opposite the first side;
forming a multi-layered transducer membrane over the first side of the wafer, one of the layers of the transducer membrane being a piezoelectric layer;
forming a well in the wafer, the well being open to the second side;
dispensing an epoxy material having a viscosity between 1 cP and 10,000 cP onto a sidewall of the well using a needle or syringe in a manner so as to induce a capillary effect that causes the epoxy material to wick down the sidewall, across a back side of the transducer membrane exposed by the well, and up a second opposing sidewall of the well such that the well is partially filled substantially without air bubbles;
deflecting the transducer membrane by applying pressurized air from the first side until the transducer membrane achieves an arcuate shape; and
curing the epoxy material while the transducer membrane is deflected.

17. The method of claim 16, wherein the deflecting and the curing are performed inside a transducer shaping apparatus.

18. The method of claim 16, further comprising thinning the wafer from the second side after the curing of the epoxy material.

19. The method of claim 16, wherein the dispensing is performed such that a predetermined amount of headspace is reserved in the well.

20. The method of claim 16, wherein dispensing the epoxy material onto the sidewall includes positioning a tip of the needle or syringe in physical contact with the sidewall.

21. The method of claim 16, wherein dispensing the epoxy material onto the sidewall includes adjusting a vertical position of a tip of the needle or syringe within the well.

22. The method of claim 16, wherein deflecting the transducer membrane occurs after dispensing the epoxy material such that the well is partially filled.

* * * * *